(12) United States Patent
DuBois et al.

(10) Patent No.: US 8,119,636 B2
(45) Date of Patent: Feb. 21, 2012

(54) PYRROLOPYRAZINE KINASE INHIBITORS

(75) Inventors: Daisy Joe DuBois, Palo Alto, CA (US); Todd Richard Elworthy, Los Altos, CA (US); Robert Than Hendricks, San Carlos, CA (US); Johannes Cornelius Hermann, San Francisco, CA (US); Rama K. Kondru, Sunnyvale, CA (US); Yan Lou, San Jose, CA (US); Timothy D. Owens, Mountain View, CA (US); David Bernard Smith, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 36 days.

(21) Appl. No.: 12/378,837

(22) Filed: Feb. 20, 2009

(65) Prior Publication Data

US 2009/0215785 A1    Aug. 27, 2009

Related U.S. Application Data

(60) Provisional application No. 61/031,035, filed on Feb. 25, 2008, provisional application No. 61/146,514, filed on Jan. 22, 2009.

(51) Int. Cl.
*A61K 31/495* (2006.01)
(52) U.S. Cl. .................................. 514/249; 544/350
(58) Field of Classification Search ............... 514/249; 544/350
See application file for complete search history.

(56) References Cited

U.S. PATENT DOCUMENTS

| 2006/0148801 | A1 | 7/2006 | Hsieh et al. | |
| 2007/0049615 | A1 | 3/2007 | Ibrahim et al. | |
| 2009/0215750 | A1* | 8/2009 | Bamberg et al. | 514/217.05 |
| 2009/0215788 | A1* | 8/2009 | Elworthy et al. | 514/250 |

FOREIGN PATENT DOCUMENTS

| WO | 0147922 A2 | 7/2001 |
| WO | 03000688 A1 | 1/2003 |
| WO | 03082868 A1 | 10/2003 |
| WO | 2008033798 A2 | 3/2008 |
| WO | 2008063888 A2 | 5/2008 |
| WO | 2008079903 A1 | 7/2008 |

OTHER PUBLICATIONS

Sablayrolles, et al. Bulletin de la Societe Chimique de France, Jul.-Aug. 1989, 467-471.*
Sablayrolles, C., et al. "Ethyl 6-methyl-5H-pyrrolo [2,3-b] pyrazine-7-carboxylate: structure and mechanism of formation from 2-aminopyrazine," US Database (Online) Chemical Abstract (1989) 77118 Abstract & Bulletin de la Societe Chimique de France.

* cited by examiner

*Primary Examiner* — James O. Wilson
*Assistant Examiner* — Douglas M Willis
(74) *Attorney, Agent, or Firm* — George W. Johnston; Dennis P. Tramaloni; Jennifer L. Kisko

(57) ABSTRACT

The present invention relates to the use of novel pyrrolopyrazine derivatives of Formula I,

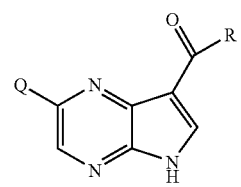

wherein the variables Q and R are defined as described herein, which inhibit JAK and SYK and are useful for the treatment of auto-immune and inflammatory diseases.

25 Claims, No Drawings

PYRROLOPYRAZINE KINASE INHIBITORS

CROSS-REFERENCE TO RELATED APPLICATIONS

This application is entitled to the benefit of U.S. provisional patent application Ser. No. 61/031,035 filed on Feb. 25, 2008 and Ser. No. 61/146,514 filed on Jan. 22, 2009, the disclosures of which are incorporated herein by reference.

FIELD OF THE INVENTION

The present invention relates to the use of novel pyrrolopyrazine derivatives which are JAK and SYK inhibitors and selectively inhibit JAK3 and are useful for the treatment of auto-immune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a γc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad.

Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (J. Immunol. 168 (2002), pp. 2475-2482). Because bone marrow transplants for SCID are curative (Blood 103 (2004), pp. 2009-2018), it seems unlikely that JAK3 has essential non-redundant functions in other tissues or organs. Hence, in contrast with other targets of immunosuppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ strains (J. Investig. Med. 44 (1996), pp. 304-311; Curr. Opin. Cell Biol. 9 (1997), pp. 233-239), the ubiquitous distribution of STATs and the fact that those molecules lack enzymatic activity that could be targeted with small-molecule inhibitors has contributed to their non-selection as key targets for immunosuppression.

SYK (Spleen Tyrosine Kinase) is a non-receptor tyrosine kinase that is essential for B-cell activation through BCR signaling. SYK become activated upon binding to phosphoryated BCR and thus initiates the early signaling events following BCR activation. Mice deficient in SYK exhibit an early block in B-cell development (Cheng et al. Nature 378: 303, 1995; Turner et al. Nature 378:298, 1995). Therefore inhibition of SYK enzymatic activity in cells is proposed as a treatment for autoimmune disease through its effects on autoantibody production.

In addition to the role of SYK in BCR signaling and B-cell activation, it also plays a key role in FcδRI mediated mast cell degranulation and eosinophil activation. Thus, SYK is implicated in allergic disorders including asthma (reviewed in Wong et al. Expert Opin Investig Drugs 13:743, 2004). SYK binds to the phosphorylated gamma chain of FcδRI via its SH2 domains and is essential for downstream signaling (Taylor et al. Mol. Cell. Biol. 15:4149, 1995). SYK deficient mast cells demonstrate defective degranulation, arachidonic acid and cytokine secretion (Costello et al. Oncogene 13:2595, 1996). This also has been shown for pharmacologic agents that inhibit SYK activity in mast cells (Yamamoto et al. J Pharmacol Exp Ther 306:1174, 2003). Treatment with SYK antisense oligonucleotides inhibits antigen-induced infiltration of eosinophils and neutrophils in an animal model of asthma (Stenton et al. J Immunol 169:1028, 2002). SYK deficient eosinophils also show impaired activation in response to FcδR stimulation (Lach-Trifilieffe et al. Blood 96:2506, 2000). Therefore, small molecule inhibitors of SYK will be useful for treatment of allergy-induced inflammatory diseases including asthma.

In view of the numerous conditions that are contemplated to benefit by treatment involving modulation of the JAK and/or SYK pathways it is immediately apparent that new compounds that modulate JAK and/or SYK pathways and methods of using these compounds should provide substantial therapeutic benefits to a wide variety of patients. Provided herein are novel pyrrolopyrazine derivatives for use in the treatment of conditions in which targeting of the JAK and/or SYK pathways or inhibition of JAK or SYK kinases, particularly JAK3, and are therapeutically useful for the treatment of auto-immune and inflammatory diseases.

SUMMARY OF THE INVENTION

The novel pyrrolopyrazine derivatives provided herein selectively inhibit JAK3 and are useful for the treatment of auto-immune and inflammatory diseases. The compounds of the invention modulate the JAK and/or SYK pathways and are useful novel pyrrolopyrazine derivatives for the treatment of auto-immune and inflammatory diseases, wherein preferred compounds selectively inhibit JAK3. For example, the compounds of the invention may inhibit JAK3 and SYK, wherein preferred compounds are selective for JAK3 of the JAK kinases and are useful novel pyrrolopyrazine derivatives for the treatment of auto-immune and inflammatory diseases. Furthermore, the compounds of the invention may inhibit JAK3 and JAK2, wherein preferred compounds are selective for JAK3 of the JAK kinases, and are useful novel pyrrolopyrazine derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazine derivatives for the treatment of auto-immune and inflammatory diseases.

The application provides a compound of Formula I

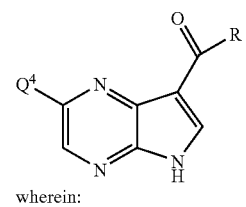

wherein:

R is $R^1$, $R^2$, $R^3$, or $R^4$;

$R^1$ is lower alkyl, lower alkoxy, phenyl, benzyl, heteroaryl, cycloalkyl, heterocycloalkyl, or cycloalkylalkyl, optionally substituted with one or more $R^{1a}$;

$R^{1a}$ is $R^{1b}$ or $R^{1c}$;

$R^{1b}$ is halogen, oxo, hydroxy, or —CN;

$R^{1c}$ is —C(=O)O($R^{1f}$), —C(=O)(CH$_2$)$_m$($R^{1e}$), —O(CH$_2$)$_m$($R^{1e}$), —S($R^{1f}$), —S(O)$_2$($R^{1f}$), or —S(=O)($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;

$R^{1d}$ is H, halogen, hydroxy, lower alkyl, amino, lower alkoxy, or lower haloalkyl;

$R^{1e}$ is H, lower alkyl, lower alkoxy, cyano, lower haloalkyl, phenyl, heteroaryl, cycloalkyl, or heterocycloalkyl;

$R^{1f}$ is H, lower alkyl, lower haloalkyl, phenyl, heteroaryl, cycloalkyl, or heterocycloalkyl;

m is 0, 1, or 2;

$R^2$ is N($R^{2a}$)$_2$;

each $R^{2a}$ is independently H or $R^{2b}$;

each $R^{2b}$ is independently lower alkyl, phenyl, heteroaryl, cycloalkyl, heterocycloalkyl, or heterocycloalkyl alkylene, optionally substituted with one or more $R^{2c}$;

$R^{2c}$ is $R^{2d}$ or $R^{2e}$;

$R^{2d}$ is halogen, oxo, or hydroxy;

$R^{2e}$ is —N($R^{2g}$)$_2$, —C(=O)($R^{2g}$), —C(=O)O($R^{2g}$), —C(=O)N($R^{2g}$)$_2$, —N($R^{2g}$)C(=O)($R^{2g}$), —S(=O)$_2$($R^{2g}$), —S(O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;

each $R^{2f}$ is independently H, halogen, lower alkyl, lower alkoxy, lower haloalkyl;

each $R^{2g}$ is independently H, lower alkyl, lower alkoxy, lower haloalkyl, or phenyl;

$R^3$ is —C(=O)$R^{3a}$;

$R^{3a}$ is lower alkyl, lower alkoxy, phenyl, or N($R^{3b}$)$_2$;

each $R^{3b}$ is independently H or lower alkyl;

$R^4$ is —O($R^{4a}$);

$R^{4a}$ is H or $R^{4b}$;

$R^{4b}$ is lower alkyl, phenyl, benzyl, lower haloalkyl, cycloalkyl, heterocycloalkyl, heteroaryl, optionally substituted with one or more $R^{4c}$;

$R^{4c}$ is halogen, hydroxy, lower alkyl, lower haloalkyl, or lower alkoxy;

$Q^4$ is $Q^{4a}$ or $Q^{4b}$;

$Q^{4a}$ is H, hydroxy, cyano, or halogen;

$Q^{4b}$ is lower alkyl, lower alkenyl, lower alkynyl, lower hydroxyalkyl, amino, or lower haloalkyl, optionally substituted with one or more $Q^{4c}$;

$Q^{4c}$ is $Q^{4d}$ or $Q^{4e}$;

each $Q^{4d}$ is independently halogen, hydroxy, or cyano;

each $Q^{4e}$ is independently lower alkyl, lower haloalkyl, lower alkoxy, amino, cycloalkyl, phenyl, heterocycloalkyl, or heteroaryl, optionally substituted with one or more $Q^{4f}$;

each $Q^{4f}$ is independently hydroxy, halogen, lower alkyl, lower alkenyl, oxo, lower haloalkyl, lower alkoxy, lower hydroxyalkyl or amino;

with the proviso that when R is $R^4$, $R^4$ is —O($R^{4a}$), $R^{4a}$ is H, and $Q^4$ is $Q^{4a}$, then $Q^{4a}$ is not H;

or a pharmaceutically acceptable salt thereof.

In one embodiment of Formula I, R is $R^1$.

In one variation of the above embodiment, $R^1$ is lower alkyl.

In one variation of the above embodiment of Formula I, the lower alkyl is tert-butyl.

In another variation of the above embodiment of Formula I, $R^1$ is —CHC(CH$_3$)$_3$.

In another variation of the above embodiment of Formula I, $R^1$ is iso-butyl.

In another variation of the above embodiment of Formula I, $R^1$ is iso-propyl.

In one embodiment of Formula I, $R^1$ is cycloalkyl.

In one embodiment of Formula I, $R^1$ is heterocycloalkyl.

In one embodiment of Formula I, $R^1$ is benzyl.

In one embodiment of Formula I, $R^1$ is phenyl.

In one embodiment of Formula I, R is $R^2$.

In one embodiment of Formula I, R is $R^2$ and $R^2$ is NH($R^{2a}$).

In one embodiment of Formula I, R is $R^2$, $R^2$ is NH($R^{2a}$) and $R^{2a}$ is $R^{2b}$.

In one embodiment of Formula I, R is $R^2$, $R^2$ is NH($R^{2a}$) and $R^{2a}$ is $R^{2b}$, and $R^{2b}$ is lower alkyl.

In one embodiment of Formula I, R is $R^2$, $R^2$ is NH($R^{2a}$) and $R^{2a}$ is $R^{2b}$, and $R^{2b}$ is iso-propyl.

In one embodiment of Formula I, R is $R^2$, $R^2$ is NH($R^{2a}$) and $R^{2a}$ is $R^{2b}$, and $R^{2b}$ is heterocycloalkyl.

In one embodiment of Formula I, R is $R^2$, $R^2$ is NH($R^{2a}$) and $R^{2a}$ is $R^{2b}$, and $R^{2b}$ is cycloalkyl.

In one embodiment of Formula I, R is $R^2$, $R^2$ is NH($R^{2a}$) and $R^{2a}$ is $R^{2b}$, and $R^{2b}$ is heterocycloalkyl alkylene.

In one embodiment of Formula I, R is $R^2$, $R^2$ is NH($R^{2a}$) and $R^{2a}$ is $R^{2b}$, and $R^{2b}$ is pyrrolidine.

In one embodiment of Formula I, R is $R^2$, $R^2$ is NH($R^{2a}$) and $R^{2a}$ is $R^{2b}$, and $R^{2b}$ is pyrrolidinyl methylene.

The application provides a compound of Formula I selected from the group consisting of:

1-(2-Bromo-5H-pyrrolo[2,3-b]pyrazin-7-yl)-3-methyl-butan-1-one;

5H-Pyrrolo[2,3-b]pyrazine-7-carboxylic acid isopropylamide;

2-Chloro-5H-pyrrolo[2,3-b]pyrazine-7-carboxylic acid isopropylamide;

2-Isopropenyl-5H-pyrrolo[2,3-b]pyrazine-7-carboxylic acid isopropylamide;

2-Isopropyl-5H-pyrrolo[2,3-b]pyrazine-7-carboxylic acid isopropylamide;

1-(2-Chloro-5H-pyrrolo[2,3-b]pyrazin-7-yl)-2,2-dimethyl-propan-1-one;

(2-Bromo-5H-pyrrolo[2,3-b]pyrazin-7-yl)-(1-methyl-cyclohexyl)-methanone;

1-(2-Bromo-5H-pyrrolo[2,3-b]pyrazin-7-yl)-2,2-dimethyl-propan-1-one;

1-(2-Isopropenyl-5H-pyrrolo[2,3-b]pyrazin-7-yl)-2,2-dimethyl-propan-1-one;

(2-Bromo-5H-pyrrolo[2,3-b]pyrazin-7-yl)-(1-methyl-cyclopentyl)-methanone;

1-(2-Ethynyl-5H-pyrrolo[2,3-b]pyrazin-7-yl)-2,2-dimethyl-propan-1-one;

1-(2-Ethyl-5H-pyrrolo[2,3-b]pyrazin-7-yl)-2,2-dimethyl-propan-1-one;

1-(2-Bromo-5H-pyrrolo[2,3-b]pyrazin-7-yl)-2,2-dimethyl-3-phenyl-propan-1-one;

1-[2-(1-Hydroxy-ethyl)-5H-pyrrolo[2,3-b]pyrazin-7-yl]-2,2-dimethyl-propan-1-one;

1-[2-(1-Hydroxy-2-methyl-propyl)-5H-pyrrolo[2,3-b]pyrazin-7-yl]-2,2-dimethyl-propan-1-one;

1-[2-(Hydroxy-o-tolyl-methyl)-5H-pyrrolo[2,3-b]pyrazin-7-yl]-2,2-dimethyl-propan-1-one;

1-[2-(Hydroxy-phenyl-methyl)-5H-pyrrolo[2,3-b]pyrazin-7-yl]-2,2-dimethyl-propan-1-one;

1-[2-(Hydroxy-pyridin-4-yl-methyl)-5H-pyrrolo[2,3-b]pyrazin-7-yl]-2,2-dimethyl-propan-1-one;

1-[2-(Hydroxy-pyridin-3-yl-methyl)-5H-pyrrolo[2,3-b]pyrazin-7-yl]-2,2-dimethyl-propan-1-one;

(2-Bromo-5H-pyrrolo[2,3-b]pyrazin-7-yl)-((3aS,6aS)-1-methyl-octahydro-pentalen-1-yl)-methanone;

(2-Bromo-5H-pyrrolo[2,3-b]pyrazin-7-yl)-((1S,2S)-1,2-dimethyl-cyclopentyl)-methanone;

(2-Bromo-5H-pyrrolo[2,3-b]pyrazin-7-yl)-(1-methyl-cyclohexyl)-methanone;

(2-Bromo-5H-pyrrolo[2,3-b]pyrazin-7-yl)-(1-methyl-cyclopentyl)-methanone;

(2-Bromo-5H-pyrrolo[2,3-b]pyrazin-7-yl)-(1-methyl-cycloheptyl)-methanone;

Adamantan-1-yl-(2-bromo-5H-pyrrolo[2,3-b]pyrazin-7-yl)-methanone;

(4-Benzyloxy-1-methyl-cyclohexyl)-(2-bromo-5H-pyrrolo[2,3-b]pyrazin-7-yl)-methanone;

(4-Benzyloxy-1-methyl-cyclohexyl)-(5H-pyrrolo[2,3-b]pyrazin-7-yl)-methanone;

1-(2-Ethynyl-5H-pyrrolo[2,3-b]pyrazin-7-yl)-2,2-dimethyl-propan-1-one;

1-(2-Isopropenyl-5H-pyrrolo[2,3-b]pyrazin-7-yl)-2,2-dimethyl-propan-1-one;

1-(2-Chloro-5H-pyrrolo[2,3-b]pyrazin-7-yl)-2,2-dimethyl-propan-1-one; and 1-(2-Bromo-5H-pyrrolo[2,3-b]pyrazin-7-yl)-3-methyl-butan-1-one.

In one embodiment, the application provides a compound of Formula I'

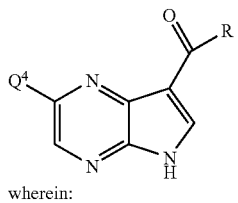

I' wherein:

R is $R^1$, $R^2$, $R^3$, or $R^4$;
$R^1$ is lower alkyl, lower alkoxy, phenyl, benzyl, heteroaryl, cycloalkyl, heterocycloalkyl, or cycloalkylalkyl, optionally substituted with one or more $R^{1a}$;
  $R^{1a}$ is $R^{1b}$ or $R^{1c}$;
    $R^{1b}$ is halogen, oxo, hydroxy, or —CN;
    $R^{1c}$ is —C(=O)O($R^{1f}$), —C(=O)(CH$_2$)$_m$($R^{1e}$), —O(CH$_2$)$_m$($R^{1e}$), —S($R^{1f}$), —S(O)$_2$($R^{1f}$), or —S(=O)($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;
      $R^{1d}$ is H, halogen, hydroxy, lower alkyl, amino, lower alkoxy, or lower haloalkyl;
      $R^{1e}$ is H, lower alkyl, lower alkoxy, cyano, lower haloalkyl, phenyl, heteroaryl, cycloalkyl, or heterocycloalkyl;
      $R^{1f}$ is H, lower alkyl, lower haloalkyl, phenyl, heteroaryl, cycloalkyl, or heterocycloalkyl;
      m is 0, 1, or 2;
$R^2$ is N($R^{2a}$)$_2$;
  each $R^{2a}$ is independently H or $R^{2b}$;
    each $R^{2b}$ is independently lower alkyl, phenyl, heteroaryl, cycloalkyl, heterocycloalkyl, or heterocycloalkyl alkylene, optionally substituted with one or more $R^{2c}$;
      $R^{2c}$ is $R^{2d}$ or $R^{2e}$;
        $R^{2d}$ is halogen, oxo, or hydroxy;
        $R^{2e}$ is —N($R^{2g}$)$_2$, —C(=O)($R^{2g}$), —C(=O)O($R^{2g}$), —C(=O)N($R^{2g}$)$_2$, —N($R^{2g}$)C(=O)($R^{2g}$), —S(=O)$_2$($R^{2g}$), —S(O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;
          each $R^{2f}$ is independently H, halogen, lower alkyl, lower alkoxy, lower haloalkyl;
          each $R^{2g}$ is independently H, lower alkyl, lower alkoxy, lower haloalkyl, or phenyl;
$R^3$ is —C(=O)$R^{3a}$;
  $R^{3a}$ is lower alkyl, lower alkoxy, phenyl, or N($R^{3b}$)$_2$;
    each $R^{3b}$ is independently H or lower alkyl;
$R^4$ is —O($R^{4a}$);
  $R^{4a}$ is H or $R^{4b}$;
    $R^{4b}$ is lower alkyl, phenyl, benzyl, lower haloalkyl, cycloalkyl, heterocycloalkyl, heteroaryl, optionally substituted with one or more $R^{4c}$;
      $R^{4c}$ is halogen, hydroxy, lower alkyl, lower haloalkyl, or lower alkoxy;
$Q^4$ is $Q^{4a}$ or $Q^{4b}$;
  $Q^{4a}$ is halogen;
  $Q^{4b}$ is lower alkyl, lower alkenyl, lower alkynyl, lower hydroxyalkyl, amino, or lower haloalkyl, optionally substituted with one or more $Q^{4c}$;
    $Q^{4c}$ is $Q^{4d}$ or $Q^{4e}$;
      each $Q^{4d}$ is independently halogen, hydroxy, or cyano;
      each $Q^{4e}$ is independently lower alkyl, lower haloalkyl, lower alkoxy, amino, cycloalkyl, phenyl, heterocycloalkyl, or heteroaryl, optionally substituted with one or more $Q^{4f}$;
        each $Q^{4f}$ is independently hydroxy, halogen, lower alkyl, lower alkenyl, oxo, lower haloalkyl, lower alkoxy, lower hydroxyalkyl or amino;
with the proviso that when R is $R^4$, $R^4$ is —O($R^{4a}$), $R^{4a}$ is H, and $Q^4$ is $Q^{4a}$, then $Q^{4a}$ is not H;
or a pharmaceutically acceptable salt thereof.

In certain embodiments of formula I, the compounds are more specifically of formula II:

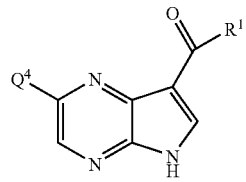

II $R^1$ is lower alkyl, lower alkoxy, phenyl, benzyl, heteroaryl, cycloalkyl, heterocycloalkyl, or cycloalkylalkyl, optionally substituted with one or more $R^{1a}$;
  $R^{1a}$ is $R^{1b}$ or $R^{1c}$;
    $R^{1b}$ is halogen, oxo, hydroxy, or —CN;
    $R^{1c}$ is —C(=O)O($R^{1f}$), —C(=O)(CH$_2$)$_m$($R^{1e}$), —O(CH$_2$)$_m$($R^{1e}$), —S($R^{1f}$), —S(O)$_2$($R^{1f}$), or —S(=O)($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;
      $R^{1d}$ is H, halogen, hydroxy, lower alkyl, amino, lower alkoxy, or lower haloalkyl;
      $R^{1e}$ is H, lower alkyl, lower alkoxy, cyano, lower haloalkyl, phenyl, heteroaryl, cycloalkyl, or heterocycloalkyl;
      $R^{1f}$ is H, lower alkyl, lower haloalkyl, phenyl, heteroaryl, cycloalkyl, or heterocycloalkyl;
      m is 0, 1, or 2; and
$Q^4$ is as defined herein.

In certain embodiments of formula II, $R^1$ is lower alkyl, preferably tert-butyl.

In certain embodiments of formula I, the compounds are more specifically of formula III:

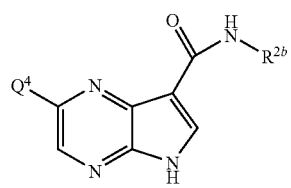

III wherein:

each $R^{2b}$ is independently lower alkyl, phenyl, heteroaryl, cycloalkyl, heterocycloalkyl, or heterocycloalkyl alkylene, optionally substituted with one or more $R^{2c}$;
  $R^{2c}$ is $R^{2d}$ or $R^{2e}$;
    $R^{2d}$ is halogen, oxo, or hydroxy;
    $R^{2e}$ is —N($R^{2g}$)$_2$, —(=O)($R^{2g}$), —C(=O)O($R^{2g}$), —C(=O)N($R^{2g}$)$_2$, —N($R^{2g}$)C(=O)($R^{2g}$), —S(=O)$_2$($R^{2g}$), —S(O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;

each $R^{2f}$ is independently H, halogen, lower alkyl, lower alkoxy, lower haloalkyl;

each $R^{2g}$ is independently H, lower alkyl, lower alkoxy, lower haloalkyl, or phenyl; and $Q^4$ is as defined herein.

In certain embodiments of formula III, $R^2$ is lower alkyl optionally substituted with one or more $R^{2c}$ as defined herein.

In certain embodiments of formula III, $R^2$ is lower alkyl.

In certain embodiments of either formulae I, II or III, $Q^4$ is H, hydroxy, cyano, or halogen, with the proviso that when R is $R^4$, $R^4$ is —O($R^{4a}$), $R^{4a}$ is H, then $Q^4$ is not H.

In certain embodiments of either formulae I, II or III, $Q^4$ is lower alkyl, lower alkenyl, lower alkynyl, lower hydroxyalkyl, amino, or lower haloalkyl, optionally substituted with one or more $Q^{4c}$ as defined herein.

In certain embodiments of either formulae I, II or III, $Q^4$ is lower alkyl, lower alkenyl, lower alkynyl, lower hydroxyalkyl, amino, or lower haloalkyl, optionally substituted with one or more lower alkyl, lower haloalkyl, lower alkoxy, amino, cycloalkyl, phenyl, heterocycloalkyl, or heteroaryl, optionally substituted with one or more $Q^{4f}$ as defined herein.

In certain embodiments of either formulae I, II or III, $Q^4$ is lower alkyl, lower alkenyl, lower alkynyl, lower hydroxyalkyl optionally substituted with one phenyl or heteroaryl, optionally substituted with one lower alkyl.

In certain embodiments of either formulae I, II or III, $Q^4$ is lower alkyl, lower alkenyl, lower alkynyl, lower hydroxyalkyl.

In one aspect, the application provides a method for treating an inflammatory and/or autoimmune condition comprising administering to a patient in need thereof a therapeutically effective amount of the compound of Formula I.

In one variation of the above method, the above method further comprises administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

In one aspect, the application provides a method for treating an inflammatory condition comprising administering to a patient in need thereof a therapeutically effective amount of the compound of Formula I, wherein R is $R^2$.

In one aspect, the application provides a method for inhibiting T-cell proliferative disorder comprising administering to a patient in need thereof a therapeutically effective amount of the compound of Formula I.

In one aspect, the application provides a method for inhibiting T-cell proliferative disorder comprising administering to a patient in need thereof a therapeutically effective amount of the compound of Formula I, wherein R is $R^2$.

In one variation of the above method, the proliferative disorder is cancer.

In one aspect, the application provides a method for treating a B-cell proliferative disorder comprising administering to a patient in need thereof a therapeutically effective amount of the compound of Formula I.

In one aspect, the application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

In one aspect, the application provides a method for preventing or treating all forms of organ rejection, including acute allograft or xenograft rejection and chronic allograft or xenograft rejection, of vascularized or non-vascularized transplants, comprising administering to a patient in need thereof a therapeutically effective amount of the compound of Formula I.

In one aspect, the application provides a method for inhibiting JAK3 activity comprising administering the compound of Formula I, wherein the compound exhibits an $IC_{50}$ of 50 micromolar or less in an in vitro biochemical assay of JAK3 activity.

In one variation of the above method, the compound exhibits an $IC_{50}$ of 100 nanomolar or less in an in vitro biochemical assay of JAK3 activity.

In one variation of the above method, the compound exhibits an $IC_{50}$ of 10 nanomolar or less in an in vitro biochemical assay of JAK3 activity.

In one aspect, the application provides a method for inhibiting SYK activity comprising administering the compound of Formula I, wherein the compound exhibits an $IC_{50}$ of 50 micromolar or less in an in vitro biochemical assay of SYK activity.

In one variation of the above method, the compound exhibits an $IC_{50}$ of 100 nanomolar or less in an in vitro biochemical assay of SYK activity.

In one variation of the above method, the compound exhibits an $IC_{50}$ of 10 nanomolar or less in an in vitro biochemical assay of SYK activity.

In one aspect, the application provides a method for treating an inflammatory condition comprising co-administering to a patient in need thereof an anti-inflammatory compound in combination with a therapeutically effective amount of the compound of Formula I.

In one aspect, the application provides a method for treating an immune disorder comprising co-administering to a patient in need thereof an immunosuppressant compound in combination with a therapeutically effective amount of the compound of Formula I.

The application provides a pharmaceutical composition comprising the compound of Formula I, admixed with at least one pharmaceutically acceptable carrier, excipient or diluent.

In one variation, the above pharmaceutical composition further comprises an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

In one aspect, the application provides a use of the compound of Formula I in the manufacture of a medicament for the treatment of an inflammatory disorder.

In one aspect, the application provides a use of the compound of Formula I in the manufacture of a medicament for the treatment of an autoimmune disorder.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, R', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ------ " drawn through a bond each refer to the point of attachment of a functional group or other chemical moiety to the rest of the molecule of which it is a part. Thus, for example:

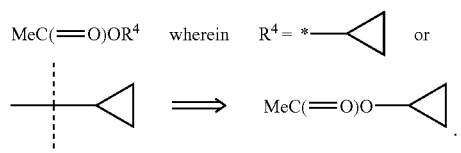

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(═O)—CH-8-C(—OH)═CH—), amide/imidic acid (—C(═O)—NH-8-C(—OH)═N—) and amidine (—C(═NR)—NH-8-C(—NHR)═N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(═O)R wherein R is hydrogen or lower alkyl as defined herein. The term or "alkylcarbonyl" as used herein denotes a group of formula C(═O)R wherein R is alkyl as defined herein. The term $C_{1-6}$ acyl refers to a group —C(═O)R containing 6 carbon atoms. The term "arylcarbonyl" as used herein means a group of formula C(═O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, adamantyl, cycloheptyl, cyclooctyl or octahydro-pentalen-1-yl. "$C_{3-7}$ cycloalkyl" as used herein refers to an cycloalkyl composed of 3 to 7 carbons in the carbocyclic ring.

The term "halogen" or "halo" as used herein means fluorine, chlorine, bromine, or iodine.

The term "heteroaryl" or "heteroaromatic" as used herein means a monocyclic, bicyclic, or tricyclic radical of 5 to 18 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole The term "heteroaryloxy" as used herein means an —O-(heteroaryl) group wherein heteroaryl is defined herein.

The term (hetero)aryl as used herein refers to an aryl or a heteroaryl moiety as each is defined herein.

The term "heterocycloalkyl", "heterocyclyl" or "heterocycle" as used herein denotes a monovalent saturated cyclic radical, consisting of one or more rings, preferably one to two rings, or three rings, of three to eight atoms per ring, incorporating one or more ring carbon atoms and one or more ring heteroatoms (chosen from N, O or S(=O)$_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "heterocycloalkyloxy" as used herein means an —O-(heterocycloalkyl) group wherein heterocycloalkyl is defined herein.

The phrase "organ rejection" includes acute allograft or xenograft rejection and chronic allograft or xenograft rejection in the setting of vascularized and/or non-vascularized (e.g. bone marrow, pancreatic islet cells) transplants.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v. 4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | SYSTEMATIC NAME | STRUCTURE | MP |
|---|---|---|---|
| I-1 | 1-(2-Bromo-5H-pyrrolo[2,3-b]pyrazin-7-yl)-3-methyl-butan-1-one | 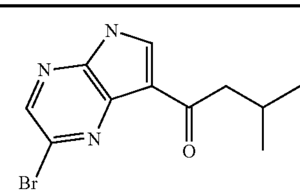 | 183-187.5 |
| I-2 | 5H-Pyrrolo[2,3-b]pyrazine-7-carboxylic acid isopropylamide | 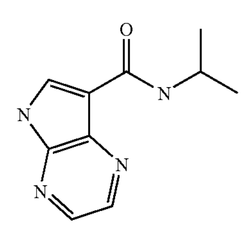 | |

TABLE I-continued

| COMPOUND | SYSTEMATIC NAME | STRUCTURE | MP |
|---|---|---|---|
| I-3 | 2-Chloro-5H-pyrrolo[2,3-b]pyrazine-7-carboxylic acid isopropylamide | 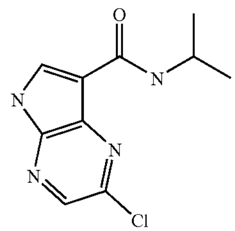 | 278-279 |
| I-4 | 2-Isopropenyl-5H-pyrrolo[2,3-b]pyrazine-7-carboxylic acid isopropylamide | 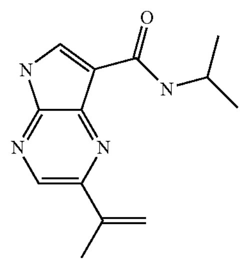 | |
| I-5 | 2-Isopropyl-5H-pyrrolo[2,3-b]pyrazine-7-carboxylic acid isopropylamide | 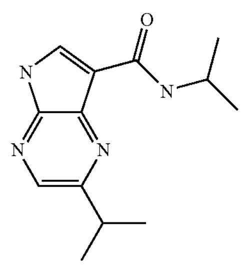 | |
| I-6 | 1-(2-Chloro-5H-pyrrolo[2,3-b]pyrazin-7-yl)-2,2-dimethyl-propan-1-one | 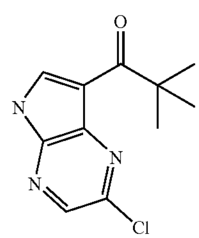 | 209-210 |
| I-7 | (2-Bromo-5H-pyrrolo[2,3-b]pyrazin-7-yl)-(1-methyl-cyclohexyl)-methanone | 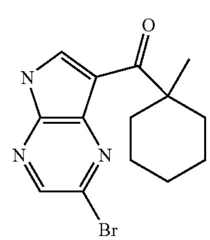 | |
| I-8 | 1-(2-Bromo-5H-pyrrolo[2,3-b]pyrazin-7-yl)-2,2-dimethyl-propan-1-one | 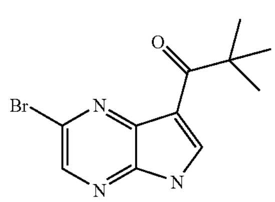 | 213.0-214.0 |

TABLE I-continued

| COMPOUND | SYSTEMATIC NAME | STRUCTURE | MP |
|---|---|---|---|
| I-9 | 1-(2-Isopropenyl-5H-pyrrolo[2,3-b]pyrazin-7-yl)-2,2-dimethyl-propan-1-one | 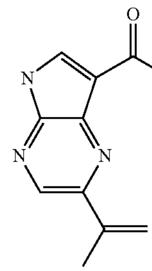 | |
| I-10 | (2-Bromo-5H-pyrrolo[2,3-b]pyrazin-7-yl)-(1-methyl-cyclopentyl)-methanone | 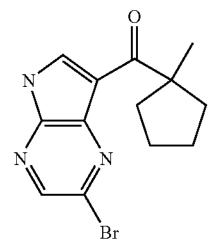 | 206.9-207.9 |
| I-11 | 1-(2-Ethynyl-5H-pyrrolo[2,3-b]pyrazin-7-yl)-2,2-dimethyl-propan-1-one | 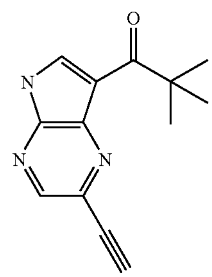 | 229.0-231.0 |
| I-12 | 1-(2-Ethyl-5H-pyrrolo[2,3-b]pyrazin-7-yl)-2,2-dimethyl-propan-1-one | 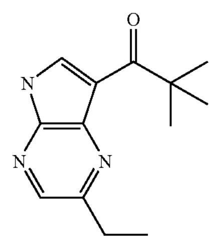 | 215.0-216.0 |
| I-13 | 1-(2-Bromo-5H-pyrrolo[2,3-b]pyrazin-7-yl)-2,2-dimethyl-3-phenyl-propan-1-one | 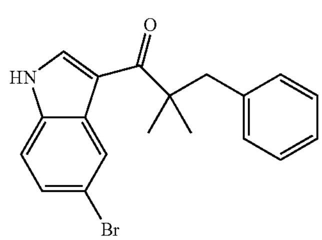 | |
| I-14 | 1-[2-(1-Hydroxy-ethyl)-5H-pyrrolo[2,3-b]pyrazin-7-yl]-2,2-dimethyl-propan-1-one | 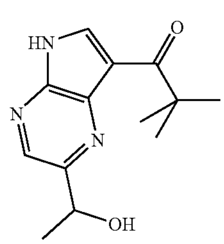 | |

TABLE I-continued

| COMPOUND | SYSTEMATIC NAME | STRUCTURE | MP |
|---|---|---|---|
| I-15 | 1-[2-(1-Hydroxy-2-methyl-propyl)-5H-pyrrolo[2,3-b]pyrazin-7-yl]-2,2-dimethyl-propan-1-one | 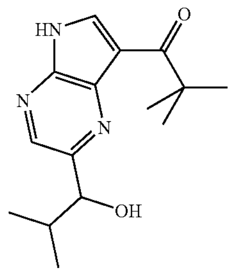 | |
| I-16 | 1-[2-(Hydroxy-o-tolyl-methyl)-5H-pyrrolo[2,3-b]pyrazin-7-yl]-2,2-dimethyl-propan-1-one | 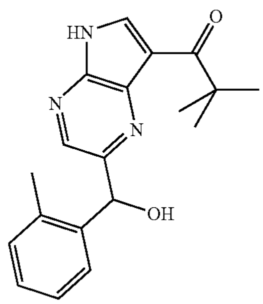 | |
| I-17 | 1-[2-(Hydroxy-phenyl-methyl)-5H-pyrrolo[2,3-b]pyrazin-7-yl]-2,2-dimethyl-propan-1-one | 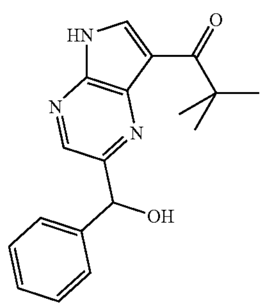 | |
| I-18 | 1-[2-(Hydroxy-pyridin-4-yl-methyl)-5H-pyrrolo[2,3-b]pyrazin-7-yl]-2,2-dimethyl-propan-1-one | 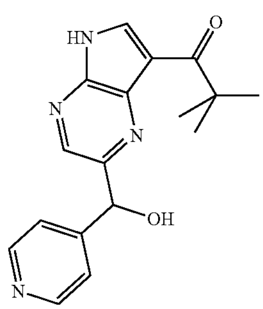 | |
| I-19 | 1-[2-(Hydroxy-pyridin-3-yl-methyl)-5H-pyrrolo[2,3-b]pyrazin-7-yl]-2,2-dimethyl-propan-1-one | 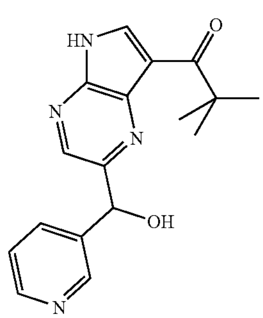 | |

TABLE I-continued

| COMPOUND | SYSTEMATIC NAME | STRUCTURE | MP |
|---|---|---|---|
| I-20 | (2-Bromo-5H-pyrrolo[2,3-b]pyrazin-7-yl)-((3aS,6aS)-1-methyl-octahydro-pentalen-1-yl)-methanone | 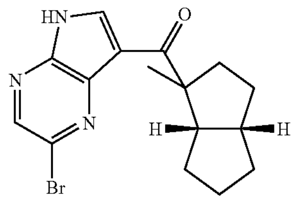 | |
| I-21 | (2-Bromo-5H-pyrrolo[2,3-b]pyrazin-7-yl)-((1S,2S)-1,2-dimethyl-cyclopentyl)-methanone | 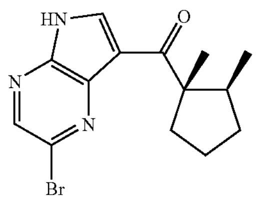 | |
| I-22 | (2-Bromo-5H-pyrrolo[2,3-b]pyrazin-7-yl)-(1-methyl-cyclohexyl)-methanone | 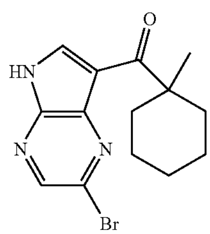 | |
| I-23 | (2-Bromo-5H-pyrrolo[2,3-b]pyrazin-7-yl)-(1-methyl-cyclopentyl)-methanone | 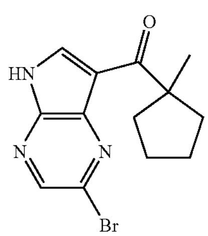 | |
| I-24 | (2-Bromo-5H-pyrrolo[2,3-b]pyrazin-7-yl)-(1-methyl-cycloheptyl)-methanone | 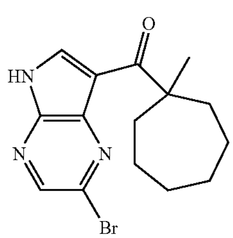 | |
| I-25 | Adamantan-1-yl-(2-bromo-5H-pyrrolo[2,3-b]pyrazin-7-yl)-methanone | 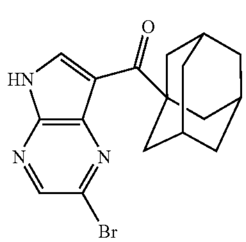 | |

TABLE I-continued

| COMPOUND | SYSTEMATIC NAME | STRUCTURE | MP |
|---|---|---|---|
| I-26 | (4-Benzyloxy-1-methyl-cyclohexyl)-(2-bromo-5H-pyrrolo[2,3-b]pyrazin-7-yl)-methanone | 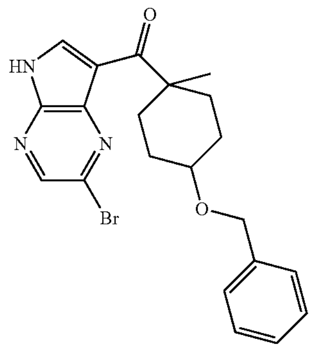 | |
| I-27 | (4-Benzyloxy-1-methyl-cyclohexyl)-(5H-pyrrolo[2,3-b]pyrazin-7-yl)-methanone | 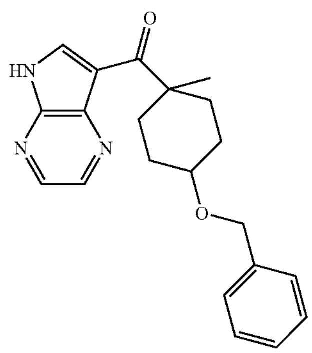 | |
| I-28 | 1-(2-Ethynyl-5H-pyrrolo[2,3-b]pyrazin-7-yl)-2,2-dimethyl-propan-1-one | 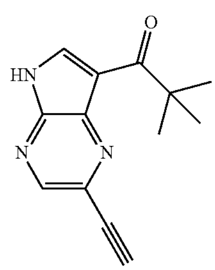 | |
| I-29 | 1-(2-Ethyl-5H-pyrrolo[2,3-b]pyrazin-7-yl)-2,2-dimethyl-propan-1-one | 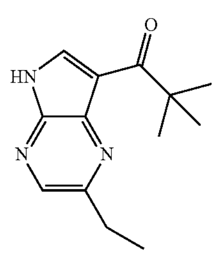 | |
| I-30 | 1-(2-Isopropenyl-5H-pyrrolo[2,3-b]pyrazin-7-yl)-2,2-dimethyl-propan-1-one | 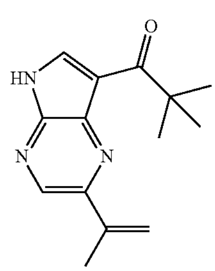 | |

TABLE I-continued

| COMPOUND | SYSTEMATIC NAME | STRUCTURE | MP |
|---|---|---|---|
| I-31 | 1-(2-Chloro-5H-pyrrolo[2,3-b]pyrazin-7-yl)-2,2-dimethyl-propan-1-one | 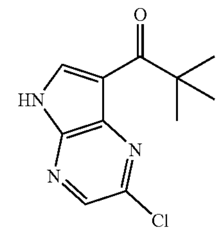 | |
| I-32 | 1-(2-Bromo-5H-pyrrolo[2,3-b]pyrazin-7-yl)-3-methyl-butan-1-one | 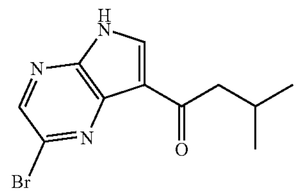 | |

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medications with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLES

Example 1

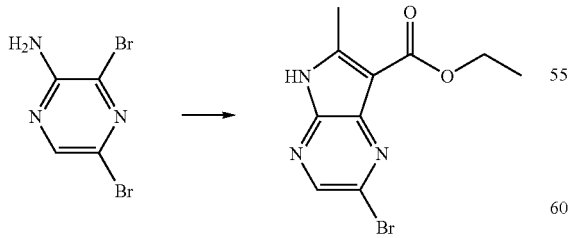

2-Bromo-6-methyl-5H-pyrrolo[2,3-b]pyrazine-7-carboxylic acid ethyl ester

To a flask charged with 20 mL of anhydrous N-methylpyrrolidine at 0° C. was added 60% NaH (840 mg, 21 mmol). After stirring 15 min, ethyl acetoacetate (2.73 g, 10.8 mmol) was added slowly. After stirring an additional 20 min 3,5-Dibromo-pyrazin-2-ylamine (5.04 g, 20 mmol). The reaction vessel was then removed from the ice bath and heated to 140° C. for 3 days. The dark mixture was cooled to rt and diluted with diethyl ether and water. The mixture was filtered and then partitioned. The organic layer was washed with water and then brine, dried over $Na_2SO_4$, filtered, and concentrated to afford a dark red oil. This was purified by silica gel chromatography (4:1 Hexanes:EtOAc) to afford 290 mg of 2-Bromo-6-methyl-5H-pyrrolo[2,3-b]pyrazine-7-carboxylic acid ethyl ester.

Example 2

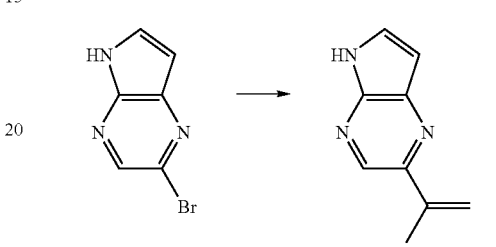

2-Isopropenyl-5H-pyrrolo[2,3-b]pyrazine

2-Isopropenyl-5H-pyrrolo[2,3b]pyrazine. 2-Bromo-5H-pyrrolo[2,3-b]pyrazine (400 mg, 2 mmol), prop-1-en-2-ylboronic acid (190 mg, 2.2 mmol), potassium carbonate (838 mg, 6 mmol) and 1,1'-bis(diphenylphosphino)ferrocene-palladium(II)dichloride (249 mg, 0.3 mmol) were combined in dioxane (40 mL) and water (10 mL) and heated at 105 C for 1 hour. The reaction mixture was poured into ethyl acetate, extracted with ethyl acetate. Then the combined extracts were washed with brine, dried ($Na_2SO_4$), filtered, and purified on silica gel to obtain 134 mg.

2-[3-(3,3-Dimethyl-pyrrolidin-1-yl)-phenyl]-5-H-pyrrolo[2,3-b]pyrazine was prepared from 2-bromo-5-H-pyrrolo[2,3-b]pyrazine following general procedures described in these Examples.

Example 3

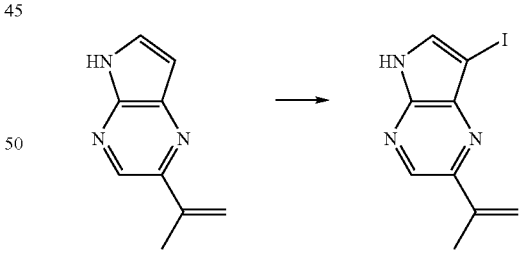

7-Iodo-2-isopropenyl-5H-pyrrolo[2,3-b]pyrazine

7-Iodo-2-isopropenyl-5H-pyrrolo[2,3b]pyrazine. 2-Isopropenyl-5H-pyrrolo[2,3b]pyrazine (89 mg, 0.56 mmol) was dissolved in DMF (5 mL) and potassium hydroxide (200 mg) was added, followed by dropwise addition of iodine (199 mg, 0.78 mmol) dissolved in DMF (1.5 mL). After stirring 3 h, the reaction was poured into water and extracted with ethyl acetate. The combined extracts were washed with water followed by brine, dried ($Na_2SO_4$), filtered, and volatiles removed under reduced pressure. The crude reaction mixture was purified on silica gel to give 92 mg.

2-[3-(3,3-Dimethyl-pyrrolidin-1-yl)-phenyl]-7-iodo-5-H-pyrrolo[2,3-b]pyrazine was prepared following general procedures described in these Examples and was TIPS protected following general procedures described in these Examples.

Example 4

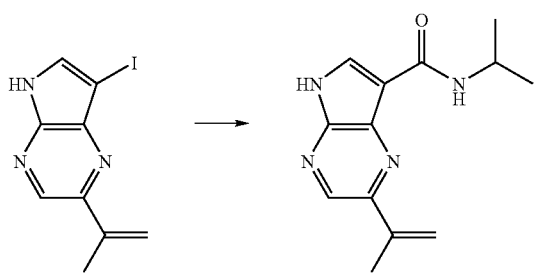

2-Isopropenyl-5H-pyrrolo[2,3-b]pyrazine-7-carboxylic acid isopropylamide

2-Isopropenyl-5H-pyrrolo[2,3b]pyrazine-7-carboxylic acid isopropylamide. 7-Iodo-2-isopropenyl-5H-pyrrolo[2,3b]pyrazine (154 mg, 0.54 mmol), palladium acetate (6 mg, 0.03 mmol) and xanthphos (17 mg, 0.03 mmol) were combined in DMF/toluene (1:3, 5 mL). The flask was purged twice with argon and then carbon monoxide was bubbled in for 1 min. Added isopropyl amine (128 mg, 2.16 mmol) and stirred for 1 hr at 100 C. After 45 min, removed volatiles under reduced pressure, partitioned the residue between ethyl acetate and water, extracted twice, dried (Na$_2$SO$_4$), filtered, and purified on silica gel to obtain 76 mg.

Example 5

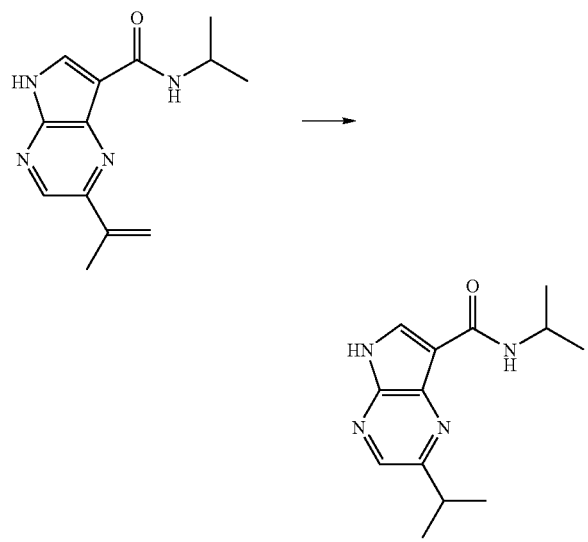

2-Isopropyl-5H-pyrrolo[2,3-b]pyrazine-7-carboxylic acid isopropylamide

2-Isopropyl-5H-pyrrolo[2,3b]pyrazine-7-carboxylic acid isopropylamide. 2-Isopropenyl-5H-pyrrolo[2,3b]pyrazine-7-carboxylic acid isopropylamide (60 mg, 0.25 mmol) was dissolved in ethanol (10 mL) and palladium on carbon was added (8 mg). The reaction mixture was shaken for 2 h on a Parr hydrogenator under 55 psi hydrogen, followed by filtration through celite. Volatiles were removed under reduced pressure to give 60 mg.

Example 6

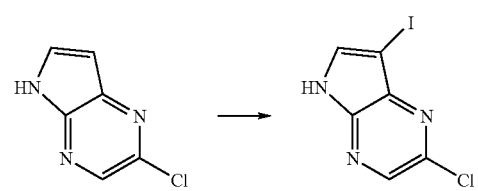

A solution of 2-Chloro-5H-pyrrolo[2,3-b]pyrazine (0.62 g, 4 mmol) in 20 mL dimethylformamide at 0° C. under argon atmosphere was treated with potassium hydroxide (0.47 g, 8.4 mmol, crushed) and iodine was added in portions (1.03 g, 4 mmol). The mixture was warmed to ambient temperature and stirred at that temperature for 10 m. The mixture was then diluted with ethyl acetate and washed with saturated aqueous sodium bisulfite. The aqueous layer was washed with ethyl acetate four times, then the combined organic layers were dried over magnesium sulfate, filtered, and concentrated to carry on to the next example.

Example 7

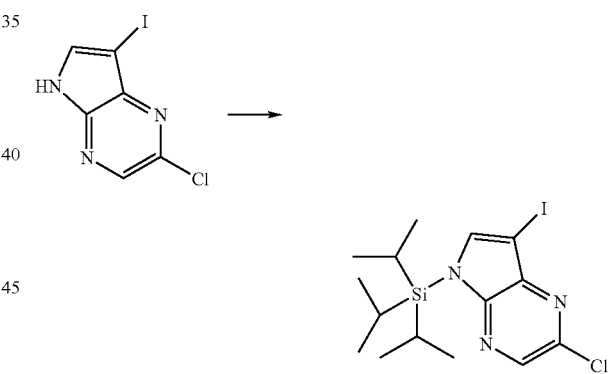

2-Chloro-7-iodo-5-triisopropylsilanyl-5H-pyrrolo[2,3-b]pyrazine

A solution of the 2-Chloro-7-iodo-5H-pyrrolo[2,3-b]pyrazine from the previous step in 30 mL of tetrahydrofuran stirring at 0° C. under argon atmosphere was treated with lithium hexamethyldisilylazide (6 mL, 1 M in hexanes, 6 mmol), followed by triisopropylsilyl chloride (1.1 mL, 5.2 mmol). After 30 m at 0° C., the solution was warmed to ambient temperature and diluted with 20% ethyl acetate in hexanes, then washed twice with water and once with brine. After drying the organic layer over magnesium sulfate, filtration was followed by solvent removal and flash chromatography of the resultant residue using 2.5% ethyl acetate in hexanes, to furnish 2-Chloro-7-iodo-5-triisopropylsilanyl-5H-pyrrolo[2,3-b]pyrazine (1.68 g, 95% over two steps).

Example 8

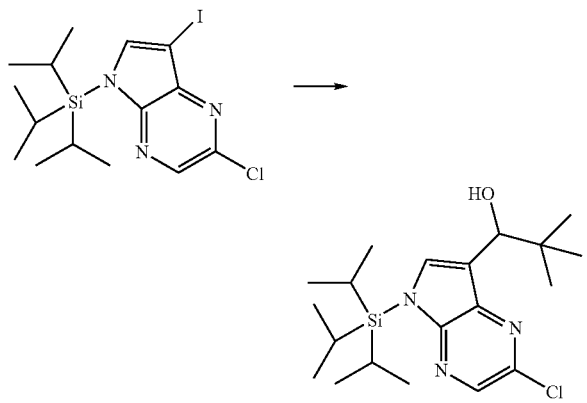

1-(2-Chloro-5-triisopropylsilanyl-5H-pyrrolo[2,3-b]pyrazin-7-yl)-2,2-dimethyl-propan-1-ol 2-Chloro-7-iodo-5-triisopropylsilanyl-5H-pyrrolo[2,3-b]pyrazine (0.56 g, 1.28 mmol) was dissolved in 10 mL of dry tetrahydrofuran and stirred under argon with cooling to −78° C. A solution of isopropylmagnesium chloride with lithium chloride (3 mL, 1M, 3 mmol) was added via syringe. After 10 m, neat pivaldehyde (0.325 mL, 3 mmol, distilled) was added all at once. After 1 h at −78° C., the reaction was quenched by the addition of saturated aqueous ammonium chloride, then diluted with ethyl acetate and allowed to warm to ambient temperature. The organic layer was then washed successively with saturated aqueous sodium bicarbonate and brine. After drying over magnesium sulfate, the solution was filtered and solvent removed, and carried directly into the next step.

Example 9

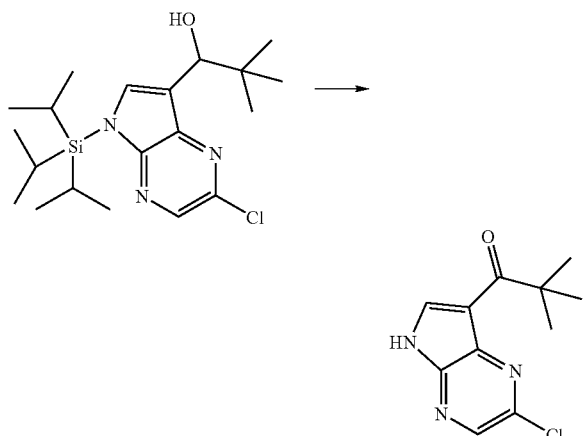

1-(2-Chloro-5H-pyrrolo[2,3-b]pyrazin-7-yl)-2,2-dimethyl-propan-1-one

The residue from the previous example was dissolved in 30 mL methylene chloride and treated with the Dess-Martin periodinane (0.76 g). After 10 m, the reaction was diluted with ethyl acetate and washed successively with saturated aqueous sodium bisulfite, saturated aqueous sodium bicarbonate and brine. After drying over magnesium sulfate, filtration, and solvent removal, the residue was taken up in 30 mL of tetrahydrofuran and treated with 10 drops each of 1 M sodium hydroxide and saturated aqueous sodium bicarbonate. The mixture was stirred for 2 h, then diluted with ethyl acetate and washed two times with saturated aqueous sodium bicarbonate and once with brine. The organic layer was dried over magnesium sulfate, filtered, and concentrated under reduced pressure. Flash chromatography using 20% ethyl acetate in hexanes then furnished the desired 1-(2-Chloro-5H-pyrrolo[2,3-b]pyrazin-7-yl)-2,2-dimethyl-propan-1-one (0.18 g, 59% for the sequence). The material was a solid, m.p. 209-210° C.

Example 10

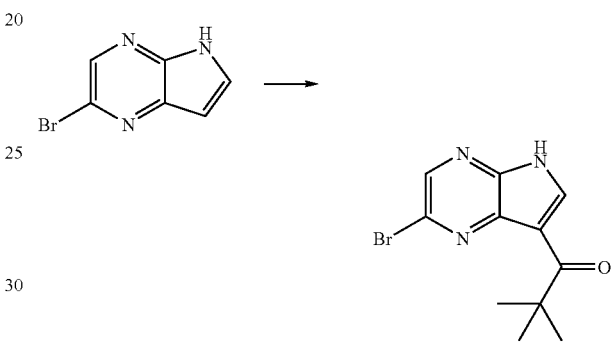

1-(2-Bromo-5H-pyrrolo[2,3-b]pyrazin-7-yl)-2,2-dimethyl-propan-1-one

To a slurry of 5-bromo-4,7-diazaindole (1.97 g, 9.95 mmol) in 40 mL of dichloromethane at 0-5° C. was added diethylaluminum chloride (1.0 M in hexane, 30 mL, 30 mmol). The reaction mixture was stirred at 0-5° C. for 30 min., then pivaloyl chloride (12 mL, 97 mmol) was added. The mixture was heated to reflux and stirred for 15 h, then cooled to 0-5° C. Sat. aq. NaHCO₃ (40 mL) was carefully added, and the mixture was then partitioned between 300 mL of a sat. aq. NaCl solution and 300 mL of ethyl acetate. The mixture was filtered through a plug of celite and the layers were separated. The aqueous layer was extracted with 300 mL of ethyl acetate. The combined organic layers were dried over MgSO₄, filtered, and concentrated to a residue. Silica gel chromatography (20->60% EtOAc/hexanes) afforded 2.50 g (89%) of 1-(2-bromo-5H-pyrrolo[2,3-b]pyrazin-7-yl)-2,2-dimethyl-propan-1-one as an off-white solid.

Example 11

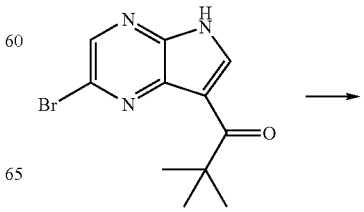

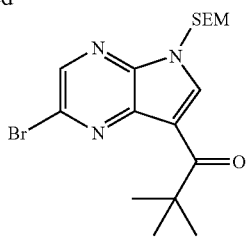

1-[2-bromo-5-(2-trimethylsilanyl-ethoxymethyl)-5H-pyrrolo[2,3-b]pyrazin-7-yl]-2,2-dimethyl-propan-1-one Sodium hydride (60% in mineral oil, 0.019 g, 0.48 mmol) was added to a stirring solution of 1-(2-bromo-5H-pyrrolo[2,3-b]pyrazin-7-yl)-2,2-dimethyl-propan-1-one (0.094 g, 0.33 mmol) in 1.5 mL of N,N'-dimethylformamide at 0-5° C. The bubbling yellow mixture was stirred at 0-5° C. for 15 min., then 2-(trimethylsilyl)ethoxymethyl chloride (0.075 mL, 0.42 mmol) was added. The resulting cloudy yellow mixture was stirred at RT for 3 h, then partitioned between 10 mL of water and 10 mL of ethyl acetate. The organic layer was sequentially washed with two 10 mL portions of water and 10 mL of a sat. aq. NaCl solution, dried over MgSO₄, filtered, and concentrated to an orange oil. Silica gel chromatography (10% EtOAc/hexanes) afforded 0.129 g (93%) of slightly impure 1-[2-bromo-5-(2-trimethylsilanyl-ethoxymethyl)-5H-pyrrolo[2,3-b]pyrazin-7-yl]-2,2-dimethyl-propan-1-one as a yellow oil that was used without further purification.

Example 12

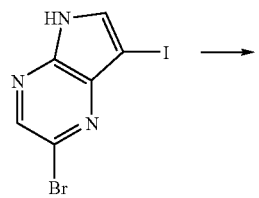

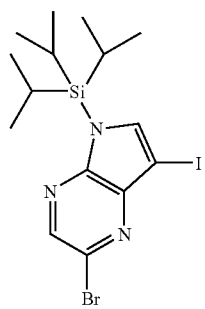

2-bromo-7-iodo-5-triisopropylsilanyl-5H-pyrrolo[2,3-b]pyrazine. 2.4 g of 2-bromo-7-iodo-5H-pyrrolo[2,3-b]pyrazine (7.4 mmol, 1 eq) was dissolved in 74 ml of tetrahydrofuran. The reaction flask was cooled in an ice bath and 8 ml lithium bis(trimethylsilyl)amide (1M hexanes solution, 8 mmol, 1.08 eq) was added dropwise. The reaction solution was stirred at room temperature for 20 min. The reaction was cooled in an ice bath and 1.7 ml triisopropylsilyl chloride (7.94 mmol, 1.07 eq) was then added slowly. After 1 hr. at room temperature, more lithium bis(trimethylsilyl)amide (0.4 ml, 0.4 mmol, 0.05 eq) and triisopropylsilyl chloride (0.2 ml, 0.9 mmol, 0.12 eq) were added. After 1 hr. more the reaction was complete. The reaction flask was cooled in an ice bath and ethyl acetate, water and sodium bicarbonate solution were added. The layers were separated and the aqueous layer was extracted once more with ethyl acetate. The ethyl acetate layers were washed with saturated sodium chloride solution, dried over sodium sulfate, filtered and evaporated. The crude residue was purified by silica gel chromatography (ethyl acetate/hexanes) to give 2.3 g (64%) of product and 0.84 g of starting material (35%).

Example 13

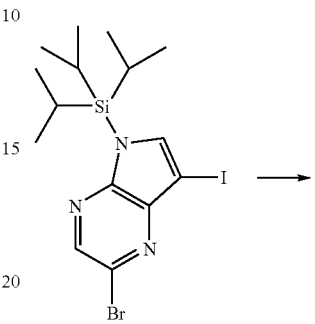

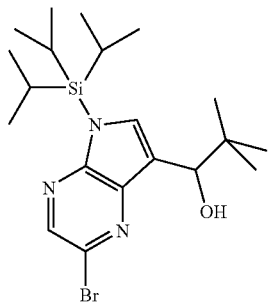

1-(2-bromo-5-triisopropylsilanyl-5H-pyrrolo[2,3-b]pyrazin-7-yl)-2,2-dimethyl-propan-1-ol. 2.05 g of 2-bromo-7-iodo-5-triisopropylsilanyl-5H-pyrrolo[2,3-b]pyrazine (4.28 mmol, 1 eq) was dissolved in 60 ml of dry tetrahydrofuran. The solution was cooled in a dry ice/acetone bath under argon. 1.91 ml of butyl lithium (2.13M hexanes solution, 4.07 mmol, 0.95 eq) was added. After 30 sec., 1.16 ml of trimethylacetaldehyde (distilled, 10.71 mmol, 2.5 eq) was quickly added. The mixture was stirred for 30 min. at −78 C, then quenched by addition of ammonium chloride solution, and then stirred to room temperature. Ethyl acetate and water were added to the reaction mixture and the layers separated. The aqueous layer was extracted once more with ethyl acetate, and the ethyl acetate layers were washed with saturated sodium chloride solution, dried over sodium sulfate, filtered and evaporated. The crude residue was purified by silica gel chromatography (ethyl acetate/hexanes) to give 0.39 g (20%) of product and 0.64 g of the product acetal (27%). Both compounds are carried into the next reaction.

Example 14

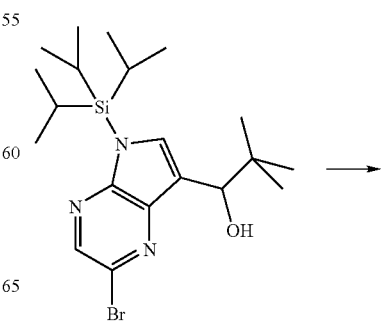

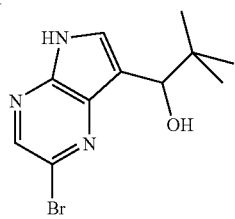

1-(2-bromo-5H-pyrrolo[2,3-b]pyrazin-7-yl)-2,2-dimethyl-propan-1-one. 0.4 g of 1-(2-bromo-5-triisopropylsilanyl-5H-pyrrolo[2,3-b]pyrazin-7-yl)-2,2-dimethyl-propan-1-ol (0.9 mmol, 1 eq) was dissolved in 9 ml of tetrahydrofuran. 1.8 ml of tetrabutylammonium fluoride (1M THF solution, 1.8 mmol, 2 eq) was added and the reaction was stirred at room temperature. After two hours, the reaction was complete and water, sodium bicarbonate solution and ethyl acetate were added. The layers were separated and the aqueous layer was extracted twice more with ethyl acetate. The ethyl acetate layers were washed with saturated sodium chloride solution, dried over sodium sulfate and evaporated to a residue.

The residue from the deprotection of 2.2 mmol of starting compound was dissolved in 22 ml of dichloromethane. 1.02 g Dess-Martin periodinane (2.4 mmol, 1.1 eq) was added and the mixture stirred at room temperature. After one hour the reaction was worked up by addition of water, sodium bicarbonate solution and ethyl acetate. The layers were separated and the aqueous layer was extracted with ethyl acetate once more. The ethyl acetate layers were washed with saturated sodium chloride solution, dried over sodium sulfate, filtered and evaporated. The crude residue was purified by silica gel chromatography (ethyl acetate/hexanes) to give 0.53 g (85%) of product.

Example 15

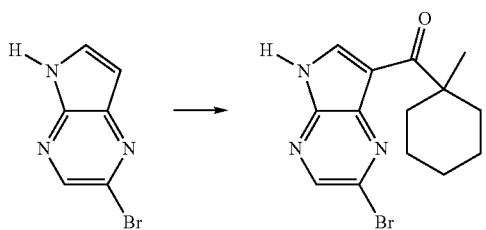

(2-Bromo-5H-pyrrolo[2,3-b]pyrazin-7-yl)-(1-methyl-cyclohexyl)-methanone

A suspension of 2-bromo-5H-pyrrolo[2,3-b]pyrazine (104 mg, 0.53 mmol) in anhydrous dichloromethane (3 ml) was cooled to 0° C. under N$_2$. Diethyl aluminum chloride (1M in hexanes, 1.57 ml, 1.57 mmol) was added quickly, and the reaction mixture was stirred for 30 minutes. 1-Methyl-cyclohexanecarbonyl chloride (844 mg, 5.3 mmol) was added dropwise, and the reaction mixture was refluxed overnight. The reaction mixture was cooled to 0° C. and quenched with saturated aqueous NaHCO$_3$. The biphasic solution was concentrated, and the remaining aqueous solution was extracted with ethyl acetate (3×). The organic layers were collected, dried over MgSO$_4$, filtered, and concentrated giving a greenish oil. The residue was purified by silica gel chromatography using 20-50% EtOAc in hexanes as eluant to provide 144 mg (85%) of (2-bromo-5H-pyrrolo[2,3-b]pyrazin-7-yl)-(1-methyl-cyclohexyl)-methanone as a light yellow solid. MP 198-199° C., M+H=322.

Example 16

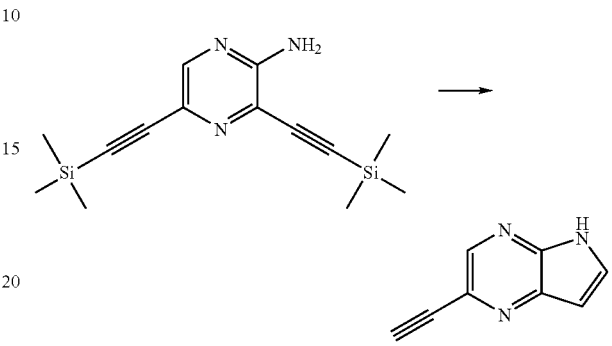

Potassium tert-butoxide (1.0 M in tetrahydrofuran, 45.6 mL, 45.6 mmol) was added dropwise to a solution of 3,5-bis-trimethylsilanylethynyl-pyrazin-2-ylamine (4.36 g, 15.2 mmol) in 60 mL of tetrahydrofuran. The reaction mixture was heated to reflux and stirred for 15 h, allowed to cool to RT, then treated with 100 mL of water. The resulting mixture was diluted with 250 mL of ethyl acetate and filtered through a plug of Celite, rinsing with 200 mL of ethyl acetate and 100 mL of water. The filtrate layers were separated, and the organic layer sequentially wasked with two 200 mL portions of water and 200 mL of a sat. aq. NaCl solution, dried over MgSO$_4$, filtered and concentrated to 0.911 g (42%) of 2-ethynyl-5H-pyrrolo[2,3-b]pyrazine as an impure brown solid that was used without further purification.

Example 17

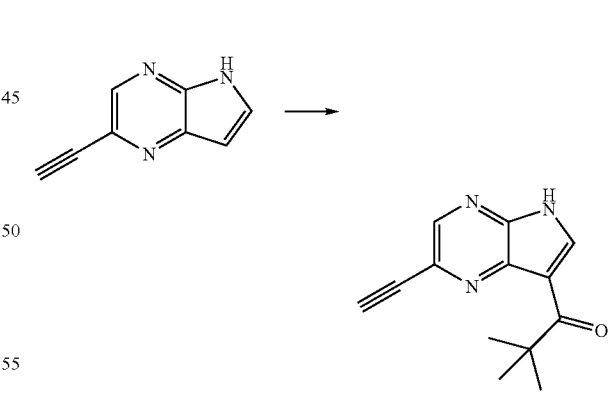

1-(2-ethynyl-5H-pyrrolo[2,3-b]pyrazin-7-yl)-2,2-dimethyl-propan-1-one

Diethylaluminum chloride (1.0 M in hexanes, 19.1 mL, 19.1 mmol) was added to a suspension of impure 2-ethynyl-5H-pyrrolo[2,3-b]pyrazine (0.911 g, 6.36 mmol) in 25 mL of dichloromethane at 0-5° C. The mixture was stirred at 0-5° C. for 30 min., then pivaloyl chloride (7.8 mL, 63.6 mmol) was slowly added. The mixture was heated to reflux and stirred for 6 h then cooled to 0-5° C. Sat. Aq. NaHCO₃ (50 mL) was carefully added, and the resulting mixture was diluted with 100 mL of ethyl acetate and filtered through a plug of Celite, rinsing with ethyl acetate and water. The filtrate layers were separated, and the aqueous layer extracted with 250 mL of ethyl acetate. The combined organic layers were dried over MgSO₄, filtered and concentrated to a residue. Silica gel chromatography (20->60% EtOAc/hexanes) afforded 0.180 g (12%) of 1-(2-ethynyl-5H-pyrrolo[2,3-b]pyrazin-7-yl)-2,2-dimethyl-propan-1-one as a brown solid.

Example 19

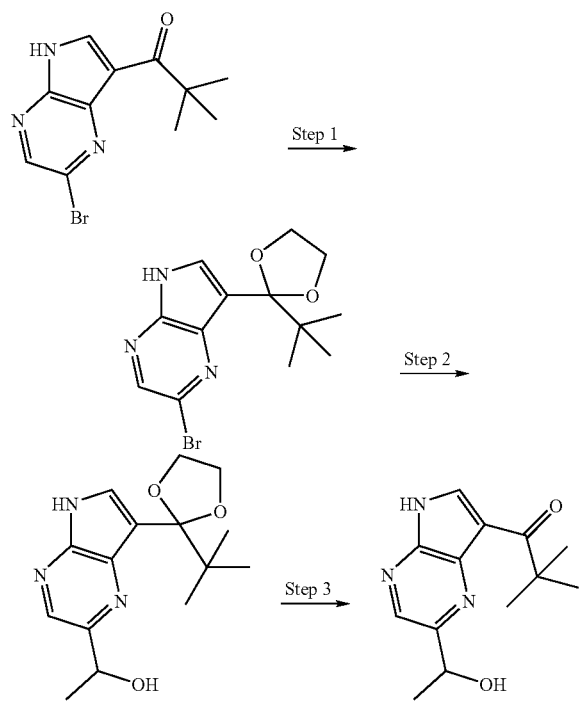

1-[2-(1-Hydroxy-ethyl)-5H-pyrrolo[2,3-b]pyrazin-7-yl]-2,2-dimethyl-propan-1-one

Step 1

1-(2-bromo-5H-pyrrolo[2,3-b]pyrazin-7-yl)-2,2-dimethyl-propan-1-one (1.5 g, 5.3 mmol) was partly dissolved in 18 ml toluene, and ethylene glycol (0.9 ml, 15.9 mmol) and then p-toluenesulfonic acid hydrate were added. The mixture was refluxed with a Dean-Stark-type trap attached for 24 hr. The reaction was cooled to room temperature and ammonium chloride solution, water and ethyl acetate were added. The layers were separated and the aqueous layer was extracted twice more with ethyl acetate. The combined ethyl acetate layers were washed with saturated sodium chloride solution and dried over sodium sulfate. After filtration and evaporation the residue was purified by silica gel chromatography(ethyl acetate/hexanes) to give 1.44 g (83%) of 2-bromo-7-(2-tert-butyl-[1,3]dioxolan-2-yl)-5H-pyrrolo[2,3-b]pyrazine.

Step 2

2-bromo-7-(2-tert-butyl-[1,3]dioxolan-2-yl)-5H-pyrrolo[2,3-b]pyrazine (0.2 g, 0.61 mmol) was dissolved in 6 ml tetrahydrofuran. Sodium hydride (49 mg, 1.22 mmol, 60% mineral oil dispersion) was added and the mixture stirred for 15 min. The mixture was cooled in a dry ice/acetone bath and butyl lithium (0.37 ml, 0.92 mmol, 2.5M hexanes solution) was added slowly. After 5 min, acetaldehyde (85 ul, 1.52 mmol) was added. After a further 1 hr, ammonium chloride solution was added, then water and ethyl acetate. The layers were separated and the aqueous layer was extracted once more with ethyl acetate. The combined ethyl acetate layers were washed with saturated sodium chloride solution and dried over sodium sulfate. After filtration and evaporation the residue was purified by silica gel chromatography(methanol/dichloromethane) to give 109 mg (61%) of 1-[7-(2-tert-butyl-[1,3]dioxolan-2-yl)-5H-pyrrolo[2,3-b]pyrazin-2-yl]-ethanol. (M+H)⁺=292.

Step 3

1-[7-(2-tert-Butyl-[1,3]dioxolan-2-yl)-5H-pyrrolo[2,3-b]pyrazin-2-yl]-ethanol (105 mg, 0.36 mmol) was dissolved in 4 ml of 1,4-dioxane. 3M hydrochloric acid (1.2 ml) was added and the mixture was stirred for 18 hr. The reaction was neutralized by addition of sodium bicarbonate solution, and ethyl acetate and water were added. The layers were separated and the aqueous layer was extracted once more with ethyl acetate. The combined ethyl acetate layers were washed with saturated sodium chloride solution and dried over sodium sulfate. After filtration and evaporation the residue was purified by silica gel chromatography(methanol/dichloromethane) and recrystallized from ethyl acetate/hexanes to give 65 mg (73%) of product. MP=152-155 C, (M+H)⁺=248.

Prepared Following General Procedures Described in these Examples:

1-[2-(1-Hydroxy-2-methyl-propyl)-5H-pyrrolo[2,3-b]pyrazin-7-yl]-2,2-dimethyl-propan-1-one. Substituting isobutyraldehyde for acetaldehyde in Step 2. MP=148-150 C, (M+H)⁺=276. 7-(2,2-Dimethyl-propionyl)-5H-pyrrolo[2,3-b]pyrazine-2-carboxylic acid isopropylamide Substituting carbon dioxide for acetaldehyde in Step 2. Then following general procedures described in these Examples, using isopropylamine and continuing with Step 3. MP=206-208 C, (M+H)⁺=289. 1-(2-Acetyl-5H-pyrrolo[2,3-b]pyrazin-7-yl)-2,2-dimethyl-propan-1-one. The product of Step 3 was treated with Dess-Martin periodinane, following general procedures described in these Examples. MP=221-223 C, (M+H)⁺=246.

1-(2-Isobutyryl-5H-pyrrolo[2,3-b]pyrazin-7-yl)-2,2-dimethyl-propan-1-one. 1-[2-(1-Hydroxy-2-methyl-propyl)-H-pyrrolo[2,3-b]pyrazin-7-yl]-2,2-dimethyl-propan-1-one was treated with Dess-Martin periodinane, following general procedures described in these Examples. MP=233-235 C, (M+H)⁺=274.

1-[2-(Hydroxy-o-tolyl-methyl)-5H-pyrrolo[2,3-b]pyrazin-7-yl]-2,2-dimethyl-propan-1-one. Substituting o-tolualdehyde for acetaldehyde in Step 2. MP=181-183 C, (M+H)⁺=324.

1-[2-(Hydroxy-phenyl-methyl)-5H-pyrrolo[2,3-b]pyrazin-7-yl]-2,2-dimethyl-propan-1-one. Substituting benzaldehyde for acetaldehyde in Step 2. MP=168-170 C, (M+H)⁺=310.

2,2-Dimethyl-1-[2-(2-methyl-benzoyl)-5H-pyrrolo[2,3-b]pyrazin-7-yl]-propan-1-one. 1-[2-(Hydroxy-o-tolyl-methyl)-5H-pyrrolo[2,3-b]pyrazin-7-yl]-2,2-dimethyl-propan-1-one was treated with Dess-Martin periodinane, following general procedures described in these Examples. MP=152-154 C, (M+H)⁺=322.

1-(2-Benzoyl-5H-pyrrolo[2,3-b]pyrazin-7-yl)-2,2-dimethyl-propan-1-one. 1-[2-(Hydroxy-phenyl-methyl)-5H-pyrrolo[2,3-b]pyrazin-7-yl]-2,2-dimethyl-propan-1-one was treated with Dess-Martin periodinane, following general procedures described in these Examples. MP=190-192, (M+H)$^+$=308.

1-[2-(Hydroxy-pyridin-4-yl-methyl)-5H-pyrrolo[2,3-b]pyrazin-7-yl]-2,2-dimethyl-propan-1-one. Substituting 4-pyridinecarboxaldehyde for acetaldehyde in Step 2. MP=189.1-194.9 C, (M+H)$^+$=311.

1-[2-(Hydroxy-pyridin-3-yl-methyl)-5H-pyrrolo[2,3-b]pyrazin-7-yl]-2,2-dimethyl-propan-1-one. Substituting 3-pyridinecarboxaldehyde for acetaldehyde in Step 2. MP=192-194 C, (M+H)$^+$=311.

2,2-Dimethyl-1-[2-(pyridine-4-carbonyl)-5H-pyrrolo[2,3-b]pyrazin-7-yl]-propan-1-one. 1-[2-(Hydroxy-pyridin-4-yl-methyl)-5H-pyrrolo[2,3-b]pyrazin-7-yl]-2,2-dimethyl-propan-1-one was treated with Dess-Martin periodinane, following general procedures described in these Examples. MP=218-220 C, (M+H)$^+$=309.

2,2-Dimethyl-1-[2-(pyridine-3-carbonyl)-5H-pyrrolo[2,3-b]pyrazin-7-yl]-propan-1-one. 1-[2-(Hydroxy-pyridin-3-yl-methyl)-5H-pyrrolo[2,3-b]pyrazin-7-yl]-2,2-dimethyl-propan-1-one was treated with Dess-Martin periodinane, following general procedures described in these Examples MP=218-220 C, (M+H)$^+$=309.

Example 20

(2-Bromo-5H-pyrrolo[2,3-b]pyrazin-7-yl)-(1-methyl-cycloheptyl)-methanone

A suspension of 2-bromo-5H-pyrrolo[2,3-b]pyrazine (100 mg, 0.505 mmol) in anhydrous dichloromethane (10 ml) was cooled to 0° C. under N$_2$. Diethyl aluminum chloride (1M in hexanes, 1.50 ml, 1.50 mmol) was added quickly, and the reaction mixture was stirred for 30 minutes. 1-Methyl-cycloheptanecarbonyl chloride (882 mg, 5.05 mmol) was added dropwise, and the reaction mixture was refluxed overnight. The reaction mixture was cooled to 0° C. and quenched with saturated aqueous NaHCO$_3$. The biphasic solution was concentrated, and the remaining aqueous solution was extracted with ethyl acetate. The organic layers were collected, dried over MgSO$_4$, filtered, and concentrated giving a pale brown solid. The residue was purified by silica gel chromatography using 19-74% EtOAc in hexanes as eluant providing 55 mg (32%) of (2-bromo-5H-pyrrolo[2,3-b]pyrazin-7-yl)-(1-methyl-cycloheptyl)-methanone as a white solid. MP 197.7-198.2° C., M+H=336.

Example 21

4-Benzyloxy-1-methyl-cyclohexanecarbonyl chloride

A solution of 4-benzyloxy-1-methyl-cyclohexanecarboxylic acid (1.71 g, 6.89 mmol) in thionyl chloride (10 ml) was refluxed for 2 hours. The reaction mixture was concentrated on high vacuum giving 1.84 g (99%) of 4-benzyloxy-1-methyl-cyclohexanecarbonyl chloride as a yellow oil.

Example 22

(4-Benzyloxy-1-methyl-cyclohexyl)-(2-bromo-5H-pyrrolo[2,3-b]pyrazin-7-yl)-methanone A solution of 2-bromo-5H-pyrrolo[2,3-b]pyrazine (531 mg, 2.68 mmol) and 4-benzyloxy-1-methyl-cyclohexanecarbonyl chloride (2.15 g, 8.05 mmol) in anhydrous Toluene (16 ml) was treated with Et$_2$AlCl (1M in Hexanes, 5.36 ml, 5.36 mmol), dropwise. The reaction mixture was stirred at 90° C. for 16 hours. The reaction mixture was cooled to room temperature, quenched with sat. NaHCO$_3$, and extracted with ethyl acetate (3×). The organic layers were collected, dried over MgSO$_4$, filtered, and concentrated giving a dark brown oil. Silica gel chromatography using 0-50% Et$_2$O in DCM as eluant provided 205 mg (18%) of (4-benzyloxy-1-methyl-cyclohexyl)-(2-bromo-5H-pyrrolo[2,3-b]pyrazin-7-yl)-methanone as a pale yellow solid. M−H=426.

Example 23

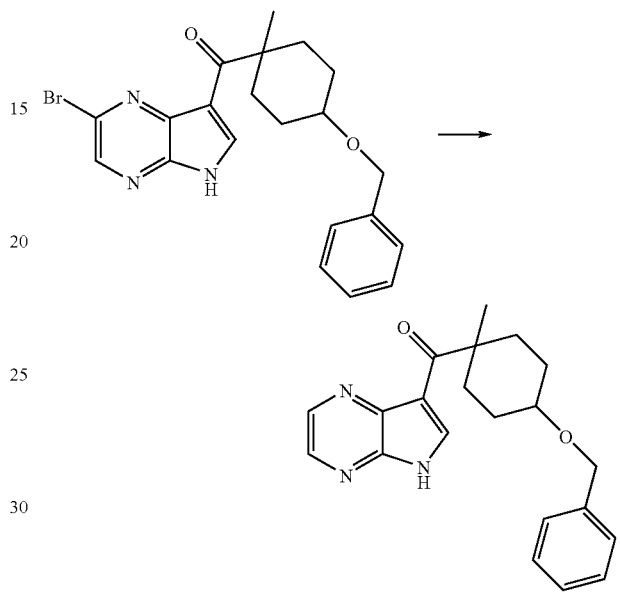

(4-Benzyloxy-1-methyl-cyclohexyl)-(5H-pyrrolo[2,3-b]pyrazin-7-yl)-methanone

A solution of (4-benzyloxy-1-methyl-cyclohexyl)-(2-bromo-5H-pyrrolo[2,3-b]pyrazin-7-yl)-methanone (13 mg, 0.03 mmol), KOH (1 mg, 0.02 mmol), and 10% Pd/C (10 mg), in EtOH (8 ml), was hydrogenated for 2 days under H$_2$ atmosphere (1 atm). The reaction mixture was filtered through a plug of celite using THF and DCM. The filtrate was concentrated to a white solid, which was purified by silica gel chromatography using 0-70% Et$_2$O in DCM as eluant providing 9 mg (82%) of (4-benzyloxy-1-methyl-cyclohexyl)-(5H-pyrrolo[2,3-b]pyrazin-7-yl)-methanone as a white solid. M+H=350.

JAK Assay Information
Determination of IC$_{50}$ of Janus Kinase (JAK) Inhibition:
  Enzymes and peptide substrate used are described below:
    JAK1: Recombinant human kinase domain from Invitrogen (Cat # PV4774)
    JAK3: Recombinant human kinase domain from Millipore (Cat #14-629) or prepared.
    JAK2: Recombinant human kinase domain from Millipore (Cat #14-640)
    Substrate: N-terminally biotinylated 14-mer peptide derived from activation loop of JAK1 with sequence of the peptide substrate: Biotin-KAIETDKEYYTVKD
  Assay conditions_used are described below:
    Assay Buffer: JAK Kinase Buffer: 50 mM Hepes [pH 7.2], 10 mM MgCl$_2$, 1 mM DTT, 1 mg/ml BSA. The assay is carried out in this buffer.
    Assay Format: The kinase activity of all three JAK kinases is measured using a radioactive, end-point assay and with trace amounts of $^{33}$P-ATP. The assays are carried out in 96-well polypropylene plates.

Experimental Method:

All concentrations are final in the reaction mixture and all incubations are carried at room temperature. Assay steps are described below:
1) Compounds are serially diluted in 100% DMSO typically at a 10× starting concentration of 1 mM. Final concentration of DMSO in the reaction is 10%.
2) Compounds are preincubated with enzyme (0.5 nM JAK3 (commercially available), 0.2 nM JAK3 (prepared), 1 nM JAK2, 5 nM JAK1) for 10 minutes.
3) Reactions are initiated by the addition of a cocktail of the two substrates (ATP and peptide premixed in the JAK Kinase Buffer). In the JAK2/JAK3 assays, ATP and the peptide are used at concentrations of 1.5 uM and 50 uM, respectively. JAK1 assay is carried out at an ATP concentration of 10 uM and a peptide concentration of 50 uM.
4) The duration of the assay for JAK2 and JAK3 is 20 minutes. JAK1 assay is carried out for 40 minutes. With all three enzymes, reactions are terminated by the addition of 0.5M EDTA to a final concentration of 100 mM.
5) 25 ul of terminated reactions are transferred to 150 ul of a 7.5% (v/v) slurry of streptavidin-coated sepharose beads in $MgCl_2$— and $CaCl_2$-free 1× Phosphate Buffered Saline containing 50 mM of EDTA in 96-well, 1.2 um MultiScreen-BV filter plates.
6) After a 30-minute incubation, the beads are washed under vacuum with the following buffers:
   a. 3 to 4 washes with 200 ul of 2M NaCl.
   b. 3 to 4 washes with 200 ul of 2M NaCl plus 1% (v/v) phosphoric acid.
   c. 1 wash with water.
7) Washed plates are dried in a 60° C. oven for between 1 to 2 hours.
8) 70 ul of Microscint 20 scintillation fluid is added to each well of filter plates and after at least 30 minutes of incubation, radioactive counts are measured in a Perkinelmer microplate scintillation counter.

Representative $IC_{50}$ results are in Table II below:

TABLE II

| Compound | $IC_{50}$ h-jak2-sf21-c | $IC_{50}$ h-jak3-sf21-c |
|---|---|---|
| I-3 | 3.5358 | 3.8826 |
| I-21 | 2.7526 | 1.493155 |
| I-25 | 1.0478 | 0.2855 |

SYK Assay Information

Determination of $IC_{50}$ of Spleen Tyrosine Kinase (SYK) Inhibition:

SYK kinase assay is a standard kinase assay adapted to a 96 well plate format. This assay is performed in 96-well format for $IC_{50}$ determination with 8 samples which represented 10 half log dilutions and a 40 μL reaction volume. The assay measures the incorporation of radiolabeled $^{33}P$ 8ATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)

Streptavidin coated beads: Streptavidin Sepharose™, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.: 0.0005 μM.

Peptide 1: biotinylated peptide is derived from a naturally occurring phosphor-acceptor consensus sequence (Biotin-EPEGDYEEVLE), special order from QCB, stock solution 20 mM, final conc.: 5.0 μM.

ATP: Adenosine-5'-triphosphate 20 mM, (ROCHE Cat. No.: 93202720), final concentration: 20 μM Buffer: HEPES: 2-Hydroxyethyl piperazine-2-ethane-sulfonic acid (Sigma, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM $MgCl_2 \times 6H_2O$: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM $MgCl_2$, 1 mM DTT, 0.1% BSA, pH 7.5

Bead wash buffer: 10 g/L PBS (Phosphate buffered saline) with 2M NaCl+1% phosphoric acid.

Experimental Method:

In 40 μL volume, 26 μL of ADB diluted, purified recombinant human SYK360-635 [0.5 nM] was mixed with 4 μL of 10× concentrations of the test compounds, [usually 100 μM-0.003 μM] in [10%] DMSO and the mixture was incubated for 10 min at RT.

The kinase reaction was initiated by the addition of 10 μL 4× substrate cocktail containing the DYE peptide substrate [0 or 5 μM], ATP [20 μM] and $^{33}$PγATP [2 μCi/rxn]. After incubation at 30° C. for 15 min, the reaction was terminated by the transfer of 25 μL of the reaction sample to a 96 well 0.65 μm Millipore MADVNOB membrane/plate containing 200 μL 5 mM EDTA and 20% Streptavidine coated beads in PBS.

The unbound radionucleotides were washed under vacuum with 3×250 μL 2M NaCl; 2×250 μL 2M NaCl+1% phosphoric acid; 1×250 μL $H_2O$. After the last wash membrane/plates were transferred to an adaptor plate, heat dried for 15 min at 60° C., and 50 μL scintillation cocktail was added to each well and 4 h later the amount of radioactivity was counted in a top counter.

The percent inhibition was calculated based on the uninhibited enzyme rate:

% Inhibition=$100/(1+(IC_{50}/\text{Inhibitor conc})^n)$

The $IC_{50}$ was calculated using a non-linear curve fit with XLfit software (ID Business Solution Ltd., Guilford, Surrey, UK).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:
1. A compound of Formula I

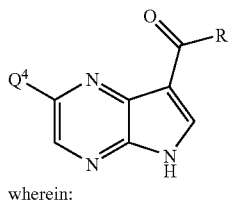

wherein:

R is $R^1$, $R^2$, $R^3$, or $R^4$;
  $R^1$ is lower alkyl, phenyl, benzyl, heteroaryl, cycloalkyl, heterocycloalkyl, or cycloalkylalkyl, optionally substituted with one or more $R^{1a}$;
   $R^{1a}$ is $R^{1b}$ or $R^{1c}$;
    $R^{1b}$ is halogen, oxo, hydroxy, or —CN;
    $R^{1c}$ is —C(=O)O($R^{1f}$), —C(=O)(CH$_2$)$_m$($R^{1e}$), —S($R^{1f}$), —S(O)$_2$($R^{1f}$), or —S(=O)($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;
    $R^{1d}$ is H, halogen, hydroxy, lower alkyl, lower alkoxy, or lower haloalkyl;
    $R^{1e}$ is H, lower alkyl, lower alkoxy, cyano, lower haloalkyl, phenyl, heteroaryl, cycloalkyl, or heterocycloalkyl;
    $R^{1f}$ is H, lower alkyl, lower haloalkyl, phenyl, heteroaryl, cycloalkyl, or heterocycloalkyl;
    m is 0, 1, or 2;
  $R^2$ is N($R^{2a}$)$_2$;
   each $R^{2a}$ is independently H or $R^{2b}$;
    each $R^{2b}$ is independently lower alkyl, phenyl, heteroaryl, cycloalkyl, heterocycloalkyl, or heterocycloalkyl alkylene, optionally substituted with one or more $R^{2c}$;
     $R^{2c}$ is $R^{2d}$ or $R^{2e}$;
      $R^{2d}$ is halogen, oxo, or hydroxy;
      $R^{2e}$ is —N($R^{2g}$)$_2$, —C(=O)($R^{2g}$), —C(=O)O($R^{2g}$), —C(=O)N($R^{2g}$)$_2$, —N($R^{2g}$)C(=O)($R^{2g}$), —S(=O)$_2$($R^{2g}$), —S(O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;
       each $R^{2f}$ is independently H, halogen, lower alkyl, lower alkoxy, lower haloalkyl;
       each $R^{2g}$ is independently H, lower alkyl, lower alkoxy, lower haloalkyl, or phenyl;
  $R^3$ is —C(=O)$R^{3a}$;
   $R^{3a}$ is lower alkyl, lower alkoxy, phenyl, or N($R^{3b}$)$_2$;
    each $R^{3b}$ is independently H or lower alkyl;
  $R^4$ is —O($R^{4a}$);
   $R^{4a}$ is H or $R^{4b}$;
    $R^{4b}$ is phenyl, benzyl, lower haloalkyl, cycloalkyl, heterocycloalkyl, heteroaryl, optionally substituted with one or more $R^{4c}$;
     $R^{4c}$ is halogen, hydroxy, lower alkyl, lower haloalkyl, or lower alkoxy;
$Q^4$ is $Q^{4a}$ or $Q^{4b}$;
 $Q^{4a}$ is H or halogen;
 $Q^{4b}$ is lower alkyl, lower alkenyl, lower alkynyl, or lower haloalkyl with the proviso that when R is $R^4$, $R^4$ is —O($R^{4a}$), $R^{4a}$ is H, and $Q^4$ is $Q^{4a}$, then $Q^{4a}$ is not H;
or a pharmaceutically acceptable salt thereof.

2. The compound of claim 1, wherein R is $R^1$.
3. The compound of claim 2, wherein $R^1$ is cycloalkyl.
4. The compound of claim 2, wherein $R^1$ is heterocycloalkyl.
5. The compound of claim 2, wherein $R^1$ is benzyl.
6. The compound of claim 2, wherein $R^1$ is phenyl.
7. The compound of claim 2, wherein $R^1$ is lower alkyl.
8. The compound of claim 7, wherein the lower alkyl is tert-butyl.
9. The compound of claim 7, wherein the lower alkyl is —CHC(CH$_3$)$_3$.
10. The compound of claim 7, wherein the lower alkyl is iso-butyl.
11. The compound of claim 7, wherein the lower alkyl is iso-propyl.
12. The compound of claim 1, wherein R is $R^2$.
13. The compound of claim 12, wherein $R^2$ is NH($R^{2a}$) and $R^{2a}$ is $R^{2b}$.
14. The compound of claim 13, wherein $R^{2b}$ is heterocycloalkyl.
15. The compound of claim 13, wherein $R^{2b}$ is cycloalkyl.
16. The compound of claim 13, wherein $R^{2b}$ is lower alkyl.
17. The compound of claim 16, wherein the lower alkyl is iso-propyl.
18. The compound of claim 13, wherein $R^{2b}$ is heterocycloalkyl alkylene.
19. The compound of claim 18, wherein the heterocycloalkyl is pyrrolidine.
20. The compound of claim 18, wherein the alkylene is methylene.
21. A pharmaceutical composition comprising the compound of claim 1, admixed with at least one pharmaceutically acceptable carrier, excipient or diluent.
22. A compound of Formula I'

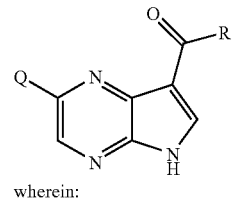

wherein:

R is $R^1$, $R^2$, $R^3$, or $R^4$;
  $R^1$ is lower alkyl, lower alkoxy, phenyl, benzyl, heteroaryl, cycloalkyl, heterocycloalkyl, or cycloalkylalkyl, optionally substituted with one or more $R^{1a}$;
   $R^{1a}$ is $R^{1b}$ or $R^{1c}$;
    $R^{1b}$ is halogen, oxo, hydroxy, or —CN;
    $R^{1c}$ is —C(=O)O($R^{1f}$), —C(=O)(CH$_2$)$_m$($R^{1e}$), —O(CH$_2$)$_m$($R^{1e}$), —S($R^{1f}$), —S(O)$_2$($R^{1f}$), or —S(=O)($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;

$R^{1d}$ is H, halogen, hydroxy, lower alkyl, amino, lower alkoxy, or lower haloalkyl;

$R^{1e}$ is H, lower alkyl, lower alkoxy, cyano, lower haloalkyl, phenyl, heteroaryl, cycloalkyl, or heterocycloalkyl;

$R^{1f}$ is H, lower alkyl, lower haloalkyl, phenyl, heteroaryl, cycloalkyl, or heterocycloalkyl;

m is 0, 1, or 2;

$R^2$ is $N(R^{2a})_2$;

each $R^{2a}$ is independently H or $R^{2b}$;

each $R^{2b}$ is independently lower alkyl, phenyl, heteroaryl, cycloalkyl, heterocycloalkyl, or heterocycloalkyl alkylene, optionally substituted with one or more $R^{2c}$;

$R^{2c}$ is $R^{2d}$ or $R^{2e}$;

$R^{2d}$ is halogen, oxo, or hydroxy;

$R^{2e}$ is $-N(R^{2g})_2$, $-C(=O)(R^{2g})$, $-C(=O)O(R^{2g})$, $-C(=O)N(R^{2g})_2$, $-N(R^{2g})C(=O)(R^{2g})$, $-S(=O)_2(R^{2g})$, $-S(O)_2N(R^{2g})_2$, lower alkyl, lower alkoxy, lower haloalkyl, phenyl, heteroaryl, heteroaryloxy, cycloalkyl, or heterocycloalkyl, optionally substituted with one or more $R^{2f}$;

each $R^{2f}$ is independently H, halogen, lower alkyl, lower alkoxy, lower haloalkyl;

each $R^{2g}$ is independently H, lower alkyl, lower alkoxy, lower haloalkyl, or phenyl;

$R^3$ is $-C(=O)R^{3a}$;

$R^{3a}$ is lower alkyl, lower alkoxy, phenyl, or $N(R^{3b})_2$;

each $R^{3b}$ is independently H or lower alkyl;

$R^4$ is $-O(R^{4a})$;

$R^{4a}$ is H or $R^{4b}$;

$R^{4b}$ is lower alkyl, phenyl, benzyl, lower haloalkyl, cycloalkyl, heterocycloalkyl, heteroaryl, optionally substituted with one or more $R^{4c}$;

$R^{4c}$ is halogen, hydroxy, lower alkyl, lower haloalkyl, or lower alkoxy;

$Q^4$ is $Q^{4b}$;

$Q^{4b}$ is lower alkyl, lower alkenyl, lower hydroxyalkyl, or lower haloalkyl, optionally substituted with one or more $Q^{4c}$;

$Q^{4c}$ is $Q^{4d}$ or $Q^{4e}$;

each $Q^{4d}$ is independently halogen, hydroxy, or cyano;

each $Q^{4e}$ is independently lower alkyl, lower haloalkyl, lower alkoxy, amino, cycloalkyl, phenyl, heterocycloalkyl, or heteroaryl, optionally substituted with one or more $Q^{4d}$;

each $Q^{4f}$ is independently hydroxy, halogen, lower alkyl, lower alkenyl, oxo, lower haloalkyl, lower alkoxy, lower hydroxyalkyl or amino;

with the proviso that when R is $R^4$, $R^4$ is $-O(R^{4a})$, $R^{4a}$ is H, and $Q^4$ is $Q^{4a}$, then $Q^{4a}$ is not H;

or a pharmaceutically acceptable salt thereof.

23. A compound of Formula I″

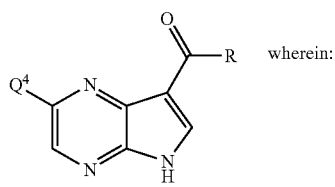

wherein:

R is $R^1$, $R^2$, $R^3$, or $R^4$;

$R^1$ is phenyl, benzyl, heteroaryl, cycloalkyl, heterocycloalkyl, or cycloalkylalkyl, optionally substituted with one or more $R^{1a}$;

$R^{1a}$ is $R^{1b}$ or $R^{1c}$;

$R^{1b}$ is halogen, oxo, hydroxy, or $-CN$;

$R^{1c}$ is $-C(=O)O(R^{1f})$, $-C(=O)(CH_2)_m(R^{1e})$, $-O(CH_2)_m(R^{1e})$, $-S(R^{1f})$, $-S(O)_2(R^{1f})$, or $-S(=O)(R^{1f})$, lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;

$R^{1d}$ is H, halogen, hydroxy, lower alkyl, amino, lower alkoxy, or lower haloalkyl;

$R^{1e}$ is H, lower alkyl, lower alkoxy, cyano, lower haloalkyl, phenyl, heteroaryl, cycloalkyl, or heterocycloalkyl;

$R^{1f}$ is H, lower alkyl, lower haloalkyl, phenyl, heteroaryl, cycloalkyl, or heterocycloalkyl;

m is 0, 1, or 2;

$R^2$ is $N(R^{2a})_2$;

each $R^{2a}$ is independently H or $R^{2b}$;

each $R^{2b}$ is independently lower alkyl, phenyl, heteroaryl, cycloalkyl, heterocycloalkyl, or heterocycloalkyl alkylene, optionally substituted with one or more $R^{2c}$;

$R^{2c}$ is $R^{2d}$ or $R^{2e}$;

$R^{2d}$ is halogen, oxo, or hydroxy;

$R^{2e}$ is $-N(R^{2g})_2$, $-C(=O)(R^{2g})$, $-C(=O)O(R^{2g})$, $-C(=O)N(R^{2g})_2$, $-N(R^{2g})C(=O)(R^{2g})$, $-S(=O)_2(R^{2g})$, $-S(O)_2N(R^{2g})_2$, lower alkyl, lower alkoxy, lower haloalkyl, phenyl, heteroaryl, heteroaryloxy, cycloalkyl, or heterocycloalkyl, optionally substituted with one or more $R^{2g}$;

each $R^{2f}$ is independently H, halogen, lower alkyl, lower alkoxy, lower haloalkyl;

each $R^{2g}$ is independently H, lower alkyl, lower alkoxy, lower haloalkyl, or phenyl;

$R^3$ is $-C(=O)R^{3a}$;

$R^{3a}$ is lower alkyl, lower alkoxy, phenyl, or $N(R^{3b})_2$;

each $R^{3b}$ is independently H or lower alkyl;

$R^4$ is $-O(R^{4a})$;

$R^{4a}$ is H or $R^{4b}$;

$R^{4a}$ is phenyl, benzyl, lower haloalkyl, cycloalkyl, heterocycloalkyl, heteroaryl, optionally substituted with one or more $R^{4c}$;

$R^{4c}$ is halogen, hydroxy, lower alkyl, lower haloalkyl, or lower alkoxy;

$Q^4$ is $Q^{4a}$ or $Q^{4b}$;

$Q^{4a}$ is H, halo, hydroxy, or cyano;

$Q^{4b}$ is lower alkyl, lower alkenyl, lower alkynyl, lower hydroxyalkyl, or lower haloalkyl, optionally substituted with one or more $Q^{4c}$;

$Q^{4c}$ is $Q^{4d}$ or $Q^{4e}$;

each $Q^{4d}$ is independently halogen, hydroxy, or cyano;

each $Q^{4e}$ is independently lower alkyl, lower haloalkyl, lower alkoxy, amino, cycloalkyl, phenyl, heterocycloalkyl, or heteroaryl, optionally substituted with one or more $Q^{4f}$;

each $Q^{4f}$ is independently hydroxy, halogen, lower alkyl, lower alkenyl, oxo, lower haloalkyl, lower alkoxy, lower hydroxyalkyl or amino;

with the proviso that when R is $R^4$, $R^4$ is $-O(R^{4a})$, $R^{4a}$ is H, and $Q^4$ is $Q^{4a}$, then $Q^{4a}$ is not H;

or a pharmaceutically acceptable salt thereof.

24. A compound selected from the group consisting of:
1-(2-Bromo-5H-pyrrolo[2,3-b]pyrazin-7-yl)-3-methyl-butan-1-one;
5H-Pyrrolo[2,3-b]pyrazine-7-carboxylic acid isopropylamide;
2-Chloro-5H-pyrrolo[2,3-b]pyrazine-7-carboxylic acid isopropylamide;
2-Isopropenyl-5H-pyrrolo[2,3-b]pyrazine-7-carboxylic acid isopropylamide;
2-Isopropyl-5H-pyrrolo[2,3-b]pyrazine-7-carboxylic acid isopropylamide;
1-(2-Chloro-5H-pyrrolo[2,3-b]pyrazin-7-yl)-2,2-dimethyl-propan-1-one;
(2-Bromo-5H-pyrrolo[2,3-b]pyrazin-7-yl)-(1-methyl-cyclohexyl)-methanone;
1-(2-Bromo-5H-pyrrolo[2,3-b]pyrazin-7-yl)-2,2-dimethyl-propan-1-one;
1-(2-Isopropenyl-5H-pyrrolo[2,3-b]pyrazin-7-yl)-2,2-dimethyl-propan-1-one;
(2-Bromo-5H-pyrrolo[2,3-b]pyrazin-7-yl)-(1-methyl-cyclopentyl)-methanone;
1-(2-Ethynyl-5H-pyrrolo[2,3-b]pyrazin-7-yl)-2,2-dimethyl-propan-1-one; and
1-(2-Ethyl-5H-pyrrolo[2,3-b]pyrazin-7-yl)-2,2-dimethyl-propan-1-one.

25. A compound selected from the group consisting of:
1-(2-Bromo-5H-pyrrolo[2,3-b]pyrazin-7-yl)-2,2-dimethyl-3-phenyl-propan-1-one;
(2-Bromo-5H-pyrrolo[2,3-b]pyrazin-7-yl)-((3aS,6aS)-1-methyl-octahydro-pentalen-1-yl)-methanone;
(2-Bromo-5H-pyrrolo[2,3-b]pyrazin-7-yl)-((1S,2S)-1,2-dimethyl-cyclopentyl)-methanone;
(2-Bromo-5H-pyrrolo[2,3-b]pyrazin-7-yl)-(1-methyl-cycloheptyl)-methanone;
Adamantan-1-yl-(2-bromo-5H-pyrrolo[2,3-b]pyrazin-7-yl)-methanone;
(4-Benzyloxy-1-methyl-cyclohexyl)-(2-bromo-5H-pyrrolo[2,3-b]pyrazin-7-yl)-methanone;
(4-Benzyloxy-1-methyl-cyclohexyl)-(5H-pyrrolo[2,3-b]pyrazin-7-yl)-methanone;
1-(2-Isopropenyl-5H-pyrrolo[2,3-b]pyrazin-7-yl)-2,2-dimethyl-propan-1-one; and
1-(2-Chloro-5H-pyrrolo[2,3-b]pyrazin-7-yl)-2,2-dimethyl-propan-1-one.

* * * * *

UNITED STATES PATENT AND TRADEMARK OFFICE
CERTIFICATE OF CORRECTION

| | | |
|---|---|---|
| PATENT NO. | : 8,119,636 B2 | Page 1 of 1 |
| APPLICATION NO. | : 12/378837 | |
| DATED | : February 21, 2012 | |
| INVENTOR(S) | : Daisy Joe DuBois et al. | |

It is certified that error appears in the above-identified patent and that said Letters Patent is hereby corrected as shown below:

Claim 22, column 49, line 15, delete "$R^{2a}$" and insert -- $R^{2c}$ --

Claim 22, column 49, line 49, delete "$Q^{4d}$;" and insert -- $Q^{4f}$; --

Claim 23, column 50, line 36, delete "$R^{2g}$" and insert -- $R^{2f}$ --

Signed and Sealed this

Seventeenth Day of April, 2012

David J. Kappos
*Director of the United States Patent and Trademark Office*